(12) United States Patent
Meesapyodsuk et al.

(10) Patent No.: US 7,923,598 B2
(45) Date of Patent: Apr. 12, 2011

(54) FATTY ACID HYDROXYLASES AND USES THEREOF

(75) Inventors: Dauenpen Meesapyodsuk, Saskatoon (CA); Xiao Qiu, Saskatoon (CA)

(73) Assignees: Bioriginal Food & Science Corp., Saskatoon (CA); University of Saskatchewan, Saskatoon (CA)

( * ) Notice: Subject to any disclaimer, the term of this patent is extended or adjusted under 35 U.S.C. 154(b) by 613 days.

(21) Appl. No.: 11/767,115

(22) Filed: Jun. 22, 2007

(65) Prior Publication Data

US 2009/0031454 A1      Jan. 29, 2009

Related U.S. Application Data

(60) Provisional application No. 60/815,774, filed on Jun. 22, 2006.

(51) Int. Cl.
*C12N 15/80*     (2006.01)
*C12N 15/81*     (2006.01)
*C12N 15/82*     (2006.01)
*C07H 21/04*     (2006.01)
*C12N 5/14*      (2006.01)

(52) U.S. Cl. ........ 800/278; 800/281; 800/298; 800/306; 800/312; 800/314; 800/320.1; 536/23.2; 536/23.74; 424/93.2; 424/93.5; 424/93.51; 435/320.1; 435/254.1; 435/254.21; 435/254.22

(58) Field of Classification Search .................... None
See application file for complete search history.

(56) References Cited

U.S. PATENT DOCUMENTS

| | | | | |
|---|---|---|---|---|
| 4,526,721 | A | * | 7/1985 | Richardson ............... 548/347.1 |
| 5,668,292 | A | * | 9/1997 | Somerville et al. ........... 800/306 |
| 7,189,559 | B2 | * | 3/2007 | Damude et al. ............. 435/254.2 |
| 2003/0159174 | A1 | | 8/2003 | Qiu |
| 2005/0216975 | A1 | | 9/2005 | Yadav et al. |

FOREIGN PATENT DOCUMENTS

| | | |
|---|---|---|
| WO | WO-96/10075 A1 | 4/1996 |
| WO | WO-03/099216 A2 | 12/2003 |

OTHER PUBLICATIONS

International Search Report for Application No. PCT/CA2007/001116, dated Oct. 12, 2007.
Written Opinion for Application No. PCT/CA2007/001116, dated Oct. 12, 2007.
Billault, I., Mantle, P.G., and Robins, R.J. (2004). Deuterium NMR used to indicate a common mechanism for the biosynthesis of ricinoleic acid by *Ricinus communis* and *Claviceps purpurea*. J. Am. Chem. Soc. 126: 3250-3256.
Broun, P., Boddupalli, S., and Somerville, C. (1998). A bifunctional oleate 12-hydroxylase: desaturase from *Lesquerella fendleri*. Plant J. 13: 201-210.
Broun, P. and Somerville, C. (1997). Accumulation of ricinoleic, lesquerolic, and densipolic acids in seeds of transgenic *Arabidopsis* plants that express a fatty acyl hydroxylase cDNA from castor bean. Plant Physiol 113: 933-942.
Jaworski, J. and Cahoon, E.B. (2003). Industrial oils from transgenic plants. Curr. Opin. Plant Biol. 6: 178-184.
Mantle, P.G. and Nisbet, L.J. (1976). Differentiation of *Claviceps purpurea* in axenic culture. J. Gen. Microbiol. 93: 321-334.
Mey, G., Oeser, B., Lebrun, M.H., and Tudzynski, P. (2002). The biotrophic, non-appressorium-forming grass pathogen *Claviceps purpurea* needs a Fus3/Pmki homologous mitogen-activated protein kinase for colonization of rye ovarian tissue. Mol. Plant Microbe Interact. 15: 303-312.
Morris, L.J., Hall, S.W., and James, A.T. (1966). The biosynthesis of ricinoleic acid by *Claviceps purpurea*. Biochem. J. 100: 29C-30C.
Smith, M.A., Moon, H., Chowrira, G., and Kunst, L. (2003). Heterologous expression of a fatty acid hydroxylase gene in developing seeds of *Arabidopsis thaliana*. Planta 217: 507-516.
Tudzynski, P., Correia, T., and Keller,U. (2001). Biotechnology and genetics of ergot alkaloids. Appl. Microbiol. Biotechnol. 57: 593-605.
van de Loo, F.J., Broun, P., Turner,S., and Somerville,C. (1995). An oleate 12-hydroxylase from *Ricinus communis*L. is a fatty acyl desaturase homolog. Proc. Natl. Acad. Sci. U. S. A 92:6743-6747.

* cited by examiner

*Primary Examiner* — Eileen B O Hara
(74) *Attorney, Agent, or Firm* — McCarter & English, LLP; Elizabeth A. Hanley, Esq.; Maneesh Gulati

(57) ABSTRACT

The invention provides isolated nucleic acid molecules which encode novel fatty acid hydroxylases. The invention also provides recombinant expression vectors including hydroxylase nucleic acid molecules, host cells into which the expression vectors have been introduced, and methods for the production of hydroxyl fatty acids such as 12-hydroxyoctadec-9-enoic acid (ricinoleic acid).

43 Claims, 7 Drawing Sheets

FIGURE 1

Sequences of *C. purpurea* oleate hydroxylase CpFAH

FIG. 1A

Nucleotide sequence (SEQ ID NO:1)

ATGGCTTCCGCTACTCCTGCAATGTCAGAAAACGCAGTTCTGCGGCACAAGGCGGCCTCGACGACTGGCATCGA
TTACGAATCGTCGGCCGCTGTCAGTCCAGCCGAATCGCCTAGAACCTCAGCCTCGTCTACATCGCTTTCGTCAC
TTTCTTCTCTCGACGCTAATGAAAAGAAAGACGAGTACGCCGGCCTCCTTGATACGTACGGAAACGCCTTCACG
CCCCCTGACTTCAGCATCAAAGACATCCGCGCTGCCATTCCCAAGCATTGCTACGAACGCTCTACCATCAAGAG
CTACGCATATGTTCTTCGCGATCTCCTCTGTCTTTCGACTACGTTCTACCTGTTCCACAACTTCGTAACGCCAG
AGAACATACCATCCAACCCCCTTCGTTTCGTGCTCTGGAGCATCTACACAGTACTGCAAGGTCTCTTTGCGACC
GGACTTTGGGTCATTGGTCATGAATGTGGTCACTGTGCCTTTTCCCCGTCTCCCTTTATCAGCGACCTCACCGG
CTGGGTCATTCACTCAGCTCTCCTCGTGCCTTATTTCAGTTGGAAATTTTCCCACAGTGCCCATCACAAGGGGA
TTGGAAACATGGAGCGCGACATGGTCTTTCTGCCTCGGACACGCGAGCAGCAGGCCACTCGACTTGGACGCGCG
GTCGAGGAACTCGGCGATCTTTGCGAGGAGACACCCATTTACACGGCTCTGCATCTGGTCGGTAAGCAGCTCAT
CGGTTGGCCCAGCTACCTCATGACGAACGCCACAGGACACAATTTCCACGAACGCCAGCGGGAGGGTCGAGGCA
AGGGCAAGAAGAACGGTTTCGGGGGGGGCGTAAATCACTTTGATCCCCGCAGCCCTATTTTCGAAGCCCGACAG
GCCAAGTACATTGTTCTCTCTGACATCGGCCTGGGTCTTGCCATCGCTGCTTTGGTATACCTCGGCAACCGATT
CGGCTGGGCCAACATGGCTGTCTGGTACTTTTTGCCCTATCTCTGGGTGAACCACTGGCTCGTTGCCATTACGT
TCCTCCAGCACACGGATCCAACTTTGCCTCATTACAATCGCGAAGAGTGGAATTTTGTTCGTGGAGGTGCTTGC
ACCATTGATCGTGACTTGGGCTTCATTGGCCGCCATCTATTCCACGGCATTGCTGATACACATGTCGTCCATCA
TTATGTCAGCCGCATTCCTTTCTATAATGCTGACGAAGCCTCCGAGGCGATCAAGCCGATCATGGGCAAGCACT
ATCGCTCAGACACCGCACACGGTCCTGTGGGATTCCTCCACGCTCTTTGGAAGACTGCTCGCTGGTGCCAGTGG
GTAGAGCCCAGCGCCGACGCCCAAGGTGCTGGCAAGGGCATCTTATTCTACCGCAACCGAAATAAACTTGGTAC
GAAGCCCATTTCAATGAAGACTCAGTAG

FIG. 1B

Protein sequence (SEQ ID NO:2)

MASATPAMSENAVLRHKAASTTGIDYESSAAVSPAESPRTSASSTSLSSLSSLDANEKKDEYAGLLDTYGNAFT
PPDFSIKDIRAAIPKHCYERSTIKSYAYVLRDLLCLSTTFYLFHNFVTPENIPSNPLRFVLWSIYTVLQGLFAT
GLWVIGHECGHCAFSPSPFISDLTGWVIHSALLVPYFSWKFSHSAHHKGIGNMERDMVFLPRTREQQATRLGRA
VEELGDLCEETPIYTALHLVGKQLIGWPSYLMTNATGHNFHERQREGRGKGKKNGFGGGVNHFDPRSPIFEARQ
AKYIVLSDIGLGLAIAALVYLGNRFGWANMAVWYFLPYLWVNHWLVAITFLQHTDPTLPHYNREEWNFVRGGAC
TIDRDLGFIGRHLFHGIADTHVVHHYVSRIPFYNADEASEAIKPIMGKHYRSDTAHGPVGFLHALWKTARWCQW
VEPSADAQGAGKGILFYRNRNKLGTKPISMKTQ

FIG. 1C

Coding Region

```
  1   M   A   S   A   T   P   A   M   S   E   N   A   V   L   R   H   K   A   A   S
  1   ATGGCTTCCGCTACTCCTGCAATGTCAGAAAACGCAGTTCTGCGGCACAAGGCGGCCTCG

21   T   T   G   I   D   Y   E   S   S   A   A   V   S   P   A   E   S   P   R   T
 61   ACGACTGGCATCGATTACGAATCGTCGGCCGCTGTCAGTCCAGCCGAATCGCCTAGAACC

41   S   A   S   S   T   S   L   S   S   L   S   S   L   D   A   N   E   K   K   D
121   TCAGCCTCGTCTACATCGCTTTCGTCACTTTCTTCTCTCGACGCTAATGAAAAGAAAGAC

61   E   Y   A   G   L   L   D   T   Y   G   N   A   F   T   P   P   D   F   S   I
181   GAGTACGCCGGCCTCCTTGATACGTACGGAAACGCCTTCACGCCCCCTGACTTCAGCATC

81   K   D   I   R   A   A   I   P   K   H   C   Y   E   R   S   T   I   K   S   Y
241   AAAGACATCCGCGCTGCCATTCCCAAGCATTGCTACGAACGCTCTACCATCAAGAGCTAC

101   A   Y   V   L   R   D   L   L   C   L   S   T   T   F   Y   L   F   H   N   F
301   GCATATGTTCTTCGCGATCTCCTCTGTCTTTCGACTACGTTCTACCTGTTCCACAACTTC

121   V   T   P   E   N   I   P   S   N   P   L   R   F   V   L   W   S   I   Y   T
361   GTAACGCCAGAGAACATACCATCCAACCCCTTCGTTTCGTGCTCTGGAGCATCTACACA

141   V   L   Q   G   L   F   A   T   G   L   W   V   I   G   H   E   C   G   H   C
421   GTACTGCAAGGTCTCTTTGCGACCGGACTTTGGGTCATTGGTCATGAATGTGGTCACTGT

161   A   F   S   P   S   P   F   I   S   D   L   T   G   W   V   I   H   S   A   L
481   GCCTTTTCCCCGTCTCCCTTTATCAGCGACCTCACCGGCTGGGTCATTCACTCAGCTCTC

181   L   V   P   Y   F   S   W   K   F   S   H   S   A   H   H   K   G   I   G   N
541   CTCGTGCCTTATTTCAGTTGGAAATTTTCCCACAGTGCCCATCACAAGGGGATTGGAAAC

201   M   E   R   D   M   V   F   L   P   R   T   R   E   Q   Q   A   T   R   L   G
601   ATGGAGCGCGACATGGTCTTTCTGCCTCGGACACGCGAGCAGCAGGCCACTCGACTTGGA

221   R   A   V   E   E   L   G   D   L   C   E   E   T   P   I   Y   T   A   L   H
661   CGCGCGGTCGAGGAACTCGGCGATCTTTGCGAGGAGACACCCATTTACACGGCTCTGCAT

241   L   V   G   K   Q   L   I   G   W   P   S   Y   L   M   T   N   A   T   G   H
721   CTGGTCGGTAAGCAGCTCATCGGTTGGCCCAGCTACCTCATGACGAACGCCACAGGACAC

261   N   F   H   E   R   Q   R   E   G   R   G   K   G   K   K   N   G   F   G   G
781   AATTTCCACGAACGCCAGCGGGAGGGTCGAGGCAAGGGCAAGAAGAACGGTTTCGGGGGG

281   G   V   N   H   F   D   P   R   S   P   I   F   E   A   R   Q   A   K   Y   I
841   GGCGTAAATCACTTTGATCCCCGCAGCCCTATTTTCGAAGCCCGACAGGCCAAGTACATT

301   V   L   S   D   I   G   L   G   L   A   I   A   A   L   V   Y   L   G   N   R
901   GTTCTCTCTGACATCGGCCTGGGTCTTGCCATCGCTGCTTTGGTATACCTCGGCAACCGA

321   F   G   W   A   N   M   A   V   W   Y   F   L   P   Y   L   W   V   N   H   W
961   TTCGGCTGGGCCAACATGGCTGTCTGGTACTTTTTGCCCTATCTCTGGGTGAACCACTGG

341   L   V   A   I   T   F   L   Q   H   T   D   P   T   L   P   H   Y   N   R   E
1021  CTCGTTGCCATTACGTTCCTCCAGCACACGGATCCAACTTTGCCTCATTACAATCGCGAA

361   E   W   N   F   V   R   G   G   A   C   T   I   D   R   D   L   G   F   I   G
1081  GAGTGGAATTTTGTTCGTGGAGGTGCTTGCACCATTGATCGTGACTTGGGCTTCATTGGC

381   R   H   L   F   H   G   I   A   D   T   H   V   V   H   H   Y   V   S   R   I
1141  CGCCATCTATTCCACGGCATTGCTGATACACATGTCGTCCATCATTATGTCAGCCGCATT

401   P   F   Y   N   A   D   E   A   S   E   A   I   K   P   I   M   G   K   H   Y
1201  CCTTTCTATAATGCTGACGAAGCCTCCGAGGCGATCAAGCCGATCATGGGCAAGCACTAT

421   R   S   D   T   A   H   G   P   V   G   F   L   H   A   L   W   K   T   A   R
1261  CGCTCAGACACCGCACACGGTCCTGTGGGATTCCTCCACGCTCTTTGGAAGACTGCTCGC

441   W   C   Q   W   V   E   P   S   A   D   A   Q   G   A   G   K   G   I   L   F
1321  TGGTGCCAGTGGGTAGAGCCCAGCGCCGACGCCCAAGGTGCTGGCAAGGGCATCTTATTC

461   Y   R   N   R   N   K   L   G   T   K   P   I   S   M   K   T   Q   -
1381  TACCGCAACCGAAATAAACTTGGTACGAAGCCCATTTCAATGAAGACTCAGTAG
```

FIGURE 2

Alignment of CpFAH and related sequences

FIGURE 3
Yeast expression of CpFAH
FIG. 3A
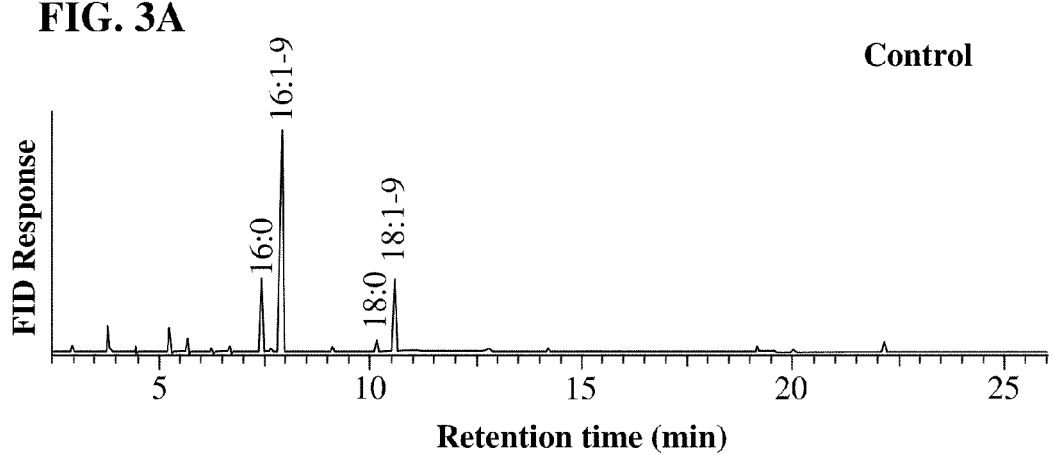
FIG. 3B
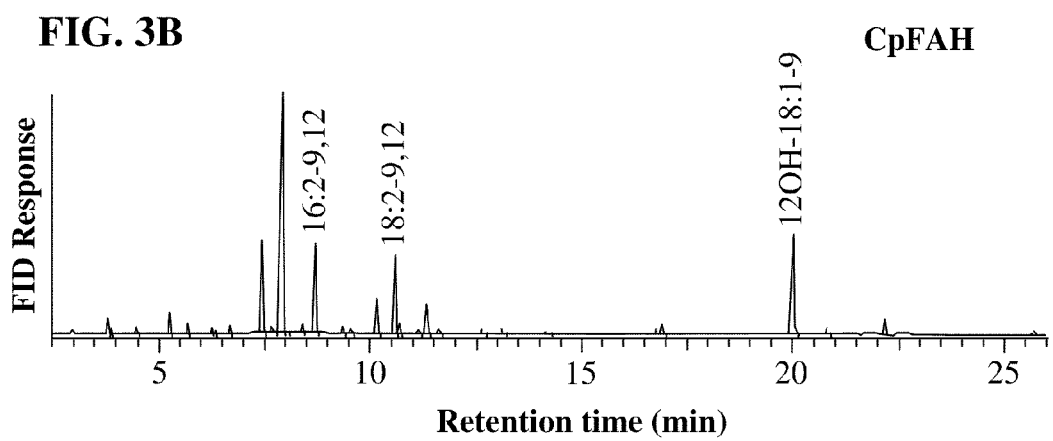

FIGURE 4
GC/MS analysis of the hydroxyl fatty acid produced by CpFAH in yeast
FIG. 4A
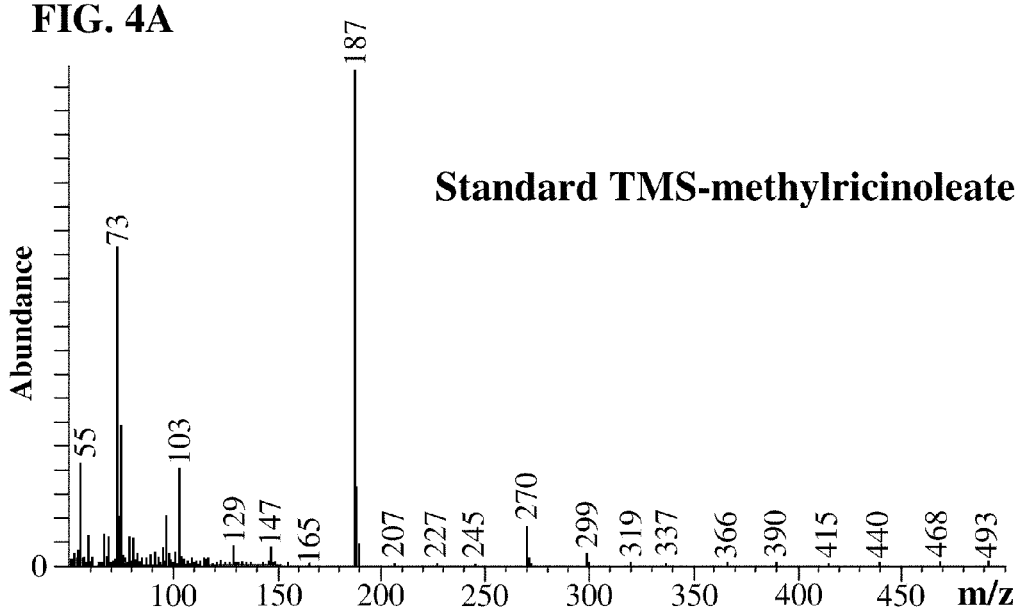
Standard TMS-methylricinoleate
FIG. 4B
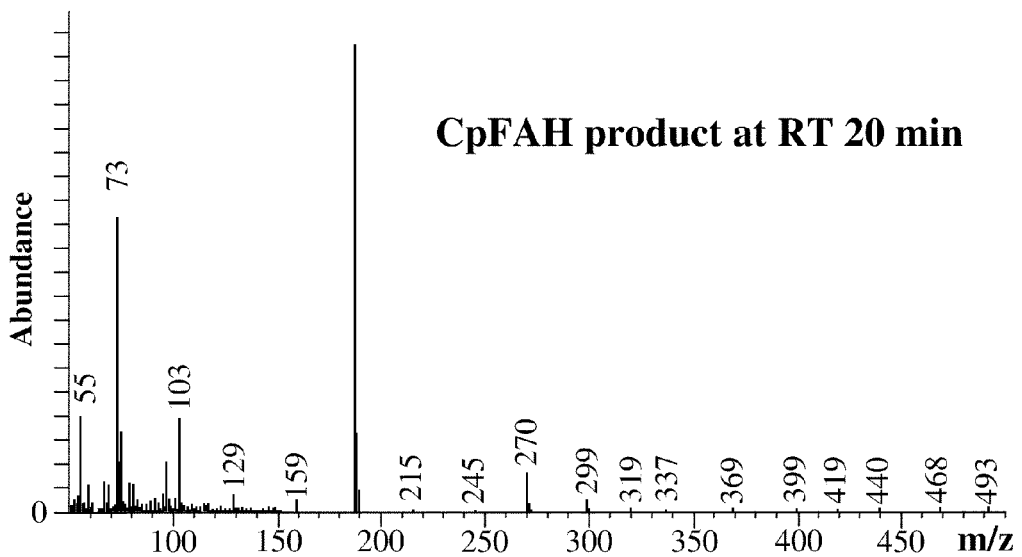
CpFAH product at RT 20 min Expression vector containing *CpFAH* for large-scale production of hydroxyl fatty acids in plants

FIGURE 6
Expression vector containing *CpFAH* for large-scale production of hydroxyl fatty acids in plants
FIG. 6A
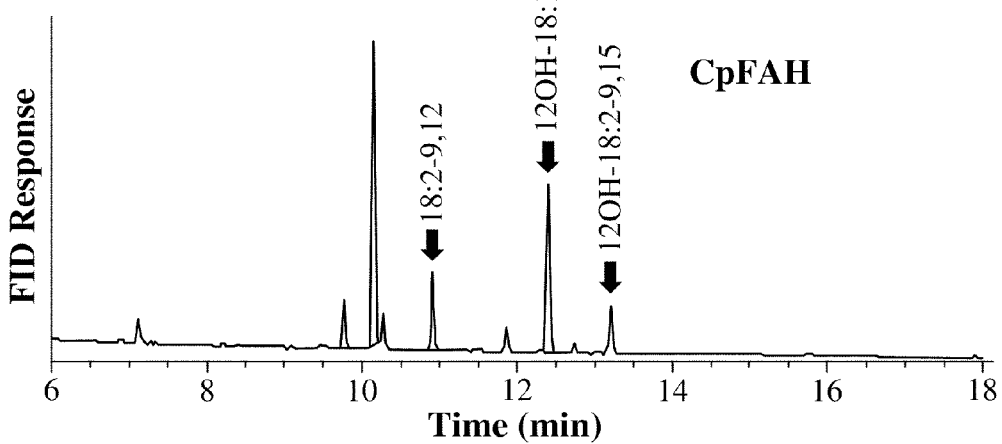
FIG. 6B
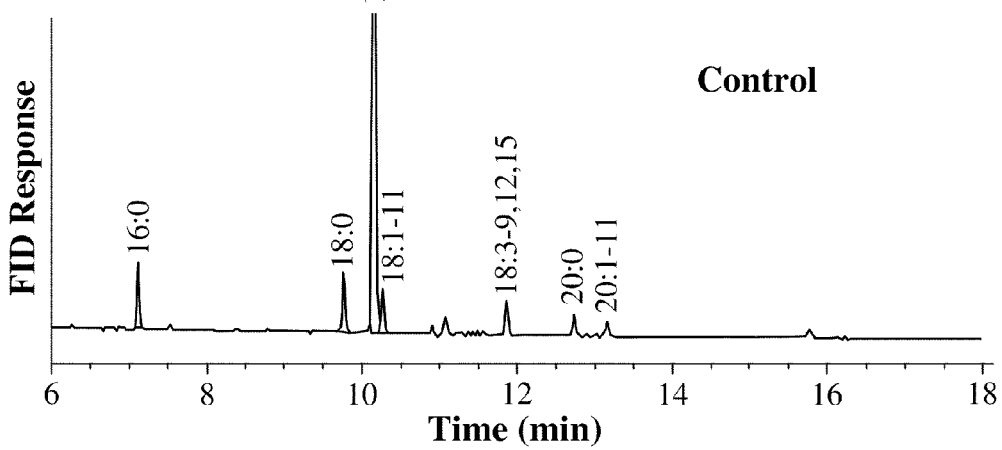

FATTY ACID HYDROXYLASES AND USES THEREOF

RELATED APPLICATIONS

This application claims priority to U.S. Provisional Application No. 60/815,774, filed Jun. 22, 2006, the entire contents of which are hereby incorporated by reference herein.

BACKGROUND OF THE INVENTION

Fatty acids are carboxylic acids with long-chain hydrocarbon side groups and play a fundamental role in many biological processes. Fatty acids are often unhydroxylated; however, such unhydroxylated fatty acids may be converted to hydroxyl fatty acids by the introduction of at least one hydroxyl group, a process catalyzed by a hydroxylase enzyme.

Hydroxyl fatty acids and hydroxyl oils are particularly important for a variety of industrial applications. Indeed, hydroxyl fatty acids, such as ricinoleic acid (12-hydroxyoctadec-9-enoic acid), are important industrial feedstock in the manufacture of biolubricants, functional fluids, ink, paints, coatings, nylons, resins, foams and other biopolymers.

The biosynthesis of fatty acids is a major activity of plants and microorganisms. Biotechnology has long been considered an efficient way to manipulate the process of producing fatty acids in plants and microorganisms. It is cost-effective and renewable with little side effects. Thus, tremendous industrial effort directed to the production of various compounds including specialty fatty acids and pharmaceutical polypeptides through the manipulation of plant, animal, and microorganismal cells has ensued.

At present, however, castor bean (*Ricinus communis*) is the only commercial source for hydroxyl fatty acids. Due to poor agronomic performance and the presence of highly potent toxins (ricin) and allergens in the seed, castor bean is not an ideal source for the fatty acids. Thus, a growing demand exists for alternatives to replace castor bean as a source of the hydroxyl fatty acids (Jaworski and Cahoon, 2003). Genes involved in the biosynthesis of hydroxyl fatty acids such as ricinoleic and lesqueroleic acids have been isolated from plant castor bean (*Ricinus communis*) and *Lesquerella fendleri* (van de Loo et al., 1995) (Broun et al., 1998). Both genes encode oleate 12-hydroxylase, which introduces a hydroxyl group at position 12 of oleic acid. However, the introduction of the castor bean oleate hydroxylase into tobacco, *Arabidopsis thaliana* resulted in low to intermediate levels of ricinoleic acid accumulation in seeds (van de Loo et al., 1995) (Broun and Somerville, 1997) (Smith et al., 2003).

Although biotechnology offers an attractive route for the production of specialty fatty acids, current techniques fail to provide an efficient means for the large scale production of hydroxyl fatty acids. Accordingly, there exists a need for an improved and efficient method of producing hydroxyl fatty acids, such as ricinoleic acid.

SUMMARY OF THE INVENTION

The present invention is based, at least in part, on the discovery of a nucleic acid molecule encoding a novel fatty acid hydroxylase from *Claviceps purpurea*. In particular, the fatty acid hydroxylase of the invention is capable of catalyzing the introduction of a hydroxyl group, for example, at position 12 of a fatty acid such as oleic acid. In a particular embodiment, the fatty acid hydroxylase is capable of catalyzing the introduction of a hydroxyl group at position 12 of octadec-9-enoic acid to form 12-hydroxyoctadec-9-enoic acid (ricinoleic acid). For example, the expression of the *Claviceps purpurea* fatty acid hydroxylase (CpFAH) in *Saccharomyces cerevisiae* resulted in the production of 12-hydroxyoctadec-9-enoic acid through the introduction of a hydroxyl group at position 12 of octadec-9-enoic acid.

The use of the nucleic acid molecules and polypeptides of the present invention provides a means for modulating, for example, enhancing, the production of desired hydroxyl fatty acids. For example, the introduction of these hydroxylase nucleic acid and polypeptide molecules in microbial and plant cells, such as *Brassica juncea*, for example, under the control of a seed-specific promoter, will allow for the enhanced production of hydroxyl fatty acids such as ricinoleic acid.

In one aspect, the present invention is directed to an isolated nucleic acid molecule selected from the group consisting of a) an isolated nucleic acid molecule encoding a fatty acid hydroxylase from the genus *Claviceps*, or a complement thereof; b) an isolated nucleic acid molecule including the nucleotide sequence of SEQ ID NO:1, or a complement thereof; c) an isolated nucleic acid molecule which encodes a polypeptide including the amino acid sequence of SEQ ID NO:2, or a complement thereof; d) an isolated nucleic acid molecule which encodes a naturally occurring allelic variant of a polypeptide including the amino acid sequence of SEQ ID NO:2, or a complement thereof; e) an isolated nucleic acid molecule including a nucleotide sequence which is at least 70% identical to the entire nucleotide sequence of SEQ ID NO:1, or a complement thereof; f) an isolated nucleic acid molecule including a nucleotide sequence which hybridizes to the complement of the nucleotide sequence of SEQ ID NO: 1 under stringent conditions, or a complement thereof; and g) an isolated nucleic acid molecule including a fragment of at least 15 contiguous nucleotides of the entire nucleotide sequence of SEQ ID NO:1, or a complement thereof. In a particular embodiment, the nucleic acid molecule encodes a fatty acid hydroxylase protein having an activity of catalyzing the introduction of a hydroxyl group in a fatty acid. Alternatively or in addition, the nucleic acid molecule encodes a protein having desaturase activity, for example, Δ12 desaturase activity. In another embodiment, the isolated nucleic acid molecule further includes a nucleotide sequence encoding a heterologous polypeptide.

In another aspect, the invention is directed to a vector, for example, an expression vector, including a nucleic acid molecule of the invention. In a particular embodiment, the nucleic acid molecule may be under the control of a seed-specific promoter, for example, Conlinin 1, Conlinin 2, napin and LuFad3.

In another aspect, the invention is directed to a host cell transfected with the expression vector including a nucleic acid molecule of the invention. The host cell may be a plant cell, for example, a plant cell from an oilseed crop, including, but not limited to, flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla. Alternatively, the host cell may be a microbial cell, including, but not limited to, *Candida, Cryptococcus, Lipomyces, Rhodosporidium, Yarrowia, Thraustochytrium, Pythium, Schizochytrium* and *Crythecodinium*.

In another aspect, the invention provides a method of producing a polypeptide by culturing a host cell of the invention in an appropriate culture medium to, thereby, produce the polypeptide, for example, a fatty acid hydroxylase.

In yet another aspect, the invention provides isolated polypeptides selected from the group consisting of a) an isolated fatty acid hydroxylase polypeptide from *Claviceps*; b) an isolated polypeptide including the amino acid sequence of SEQ ID NO:2; c) an isolated polypeptide including a naturally occurring allelic variant of a polypeptide including the amino acid sequence of SEQ ID NO:2; d) an isolated polypeptide including an amino acid sequence encoded by a nucleic acid molecule including the nucleotide sequence of SEQ ID NO: 1; e) an isolated polypeptide which is encoded by a nucleic acid molecule including a nucleotide sequence which is at least 70% identical to the entire nucleotide sequence of SEQ ID NO:1; f) an isolated polypeptide including an amino acid sequence which is at least 70% identical to the entire amino acid sequence of SEQ ID NO:2; and g) an isolated polypeptide including a fragment of a polypeptide including the amino acid sequence of SEQ ID NO:2, wherein the polypeptide fragment maintains a biological activity of the complete polypeptide. In a particular embodiment, the polypeptide is involved in the production of a hydroxyl fatty acid. Alternatively or in addition, the polypeptide has a desaturase activity, for example, a Δ12 desaturase activity. In another embodiment, the polypeptide also includes a heterologous amino acid sequence.

In another aspect, the invention provides a method for producing a hydroxyl fatty acid by culturing a host cell of the invention such that the hydroxyl fatty acid is produced. In another embodiment, the invention provides a method for producing a hydroxyl fatty acid by contacting a composition including at least one hydroxylase target molecule with at least one polypeptide of the invention under conditions such that the hydroxyl fatty acid is produced. In yet another aspect, the invention provides a method of producing a cell capable of generating a hydroxyl fatty acid by introducing into the cell a nucleic acid molecule of the invention, wherein the nucleic acid molecule encodes a hydroxylase having an activity of catalyzing the introduction of a hydroxyl group in a fatty acid. In yet another aspect, the present invention is directed to a method of modulating, for example, enhancing, the production of a hydroxyl fatty acid by culturing a cell transformed with the expression vector of the invention, such that modulation of the production of a hydroxyl fatty acid occurs. In a further aspect, the present invention is directed to a method for the large scale production of a hydroxyl fatty acid by culturing a cell transformed with the expression vector of the invention. In certain embodiments, the expression of the nucleic acid molecule results in the modulation of the production of the hydroxyl fatty acid, 12-hydroxyoctadec-9-enoic acid (ricinoleic acid). Additionally, the hydroxylase target molecule or the unhydroxylated fatty acid may be octadec-9-enoic acid (oleic acid).

In one embodiment, the hydroxyl fatty acid produced by the foregoing methods may be recovered from the culture. In another embodiment the cell is a plant cell, for example, an oilseed plant, including, but not limited to, flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla. In a particular embodiment, the cell belongs to the genus *Arabidopsis*. In another embodiment, the cell is *Brassica juncea*. In yet another embodiment, the cell is a microbial cell, for example, *Candida, Cryptococcus, Lipomyces, Rhodosporidium, Yarrowia, Thraustochytrium, Pythium, Schizochytrium* and *Cythecodinium*.

In yet another aspect, the present invention is directed to a host cell having a) a nucleic acid molecule including the nucleotide sequence of SEQ ID NO:1, wherein the nucleic acid molecule is disrupted by at least one technique selected from the group consisting of a point mutation, a truncation, an inversion, a deletion, an addition, a substitution and homologous recombination, for example, such that the fatty acid hydroxylase activity and/or desaturase activity is disrupted; b) a nucleic acid molecule having the nucleotide sequence of SEQ ID NO:1, wherein the nucleic acid molecule includes one or more nucleic acid modifications as compared to the sequence set forth in SEQ ID NO:1, wherein the modification is selected from the group consisting of a point mutation, a truncation, an inversion, a deletion, an addition and a substitution, for example, such that the modified nucleic acid molecule encodes for a polypeptide retaining fatty acid hydroxylase and/or desaturase activity; or c) a nucleic acid molecule having the nucleotide sequence of SEQ ID NO:1, wherein the regulatory region of the nucleic acid molecule is modified relative to the wild-type regulatory region of the molecule by at least one technique selected from the group consisting of a point mutation, a truncation, an inversion, a deletion, an addition, a substitution and homologous recombination, for example, so as to modify, for example, enhance fatty acid hydroxylase and/or desaturase activity.

In other aspects, the invention is directed to a plant including a vector described herein, and oils or seeds produced by the plant. In another aspect, the invention is directed to a composition including the oil and/or seed, wherein the composition comprises a product selected from the group consisting of a biolubricant, a functional fluid, an ink, a paint, a coating, a nylon, a resin, a foam and a biopolymer. In another aspect, the invention is directed to a hydroxyl fatty acid obtained by a method described herein. In a further aspect, the invention is directed to compositions including the hydroxyl fatty acids produced by a method described herein, wherein the composition is a product selected from the group consisting of a biolubricant, a functional fluid, an ink, a paint, a coating, a nylon, a resin, a foam and a biopolymer.

Other features and advantages of the invention will be apparent from the following detailed description and claims.

BRIEF DESCRIPTION OF THE DRAWINGS

FIG. 1 shows the nucleotide and amino acid sequence of an oleate hydroxylase from *Claviceps purpurea* (CpFAH) as follows: (A) the cDNA sequence of the open reading frame (SEQ ID NO:1); (B) the translated protein sequence (SEQ ID NO:2) and (C) the cDNA aligned with the translated amino acid sequence.

FIG. 2 shows an alignment of the amino acid of oleate hydroxylase from *Claviceps purpurea* (SEQ ID NO: 2) versus that of other fatty acid hydroxylases and related enzymes including those from *A. nidulans* (AnOdeA) (SEQ ID NO: 3), *Lesquerella fendleri* (LfFAH) (SEQ ID NO: 4), and *Ricinus communis* (RcFAH) (SEQ ID NO: 5).

FIG. 3B is a gas chromatographic (GC) analysis of the expression of fatty acids in an experimental strain of yeast transformed with CpFAH as compared to a control strain of yeast (FIG. 3A). The peak labeled 12OH-18:1-9 represents the presence of a fatty acid unique to the yeast strain transformed with CpFAH.

FIG. 4B is a gas chromatographic/mass spectroscopy (GC/MS) analysis of the peak unique to the experimental strain of yeast as depicted in FIG. 3B (i.e., 12OH-18:1-9) as compared to the GC/MS analysis of Standard TMS-methylricinoleate (FIG. 4A).

FIG. 6A is a gas chromatographic (GC) analysis of TMS-derivatized fatty acid methyl esters prepared from a single seed of *Arabidopsis thaliana* double mutant (fad2fae1) transformed with CpFAH as compared to a control untransformed strain of fad2fae1 (FIG. 6B).

DETAILED DESCRIPTION OF THE INVENTION

Figure 5:
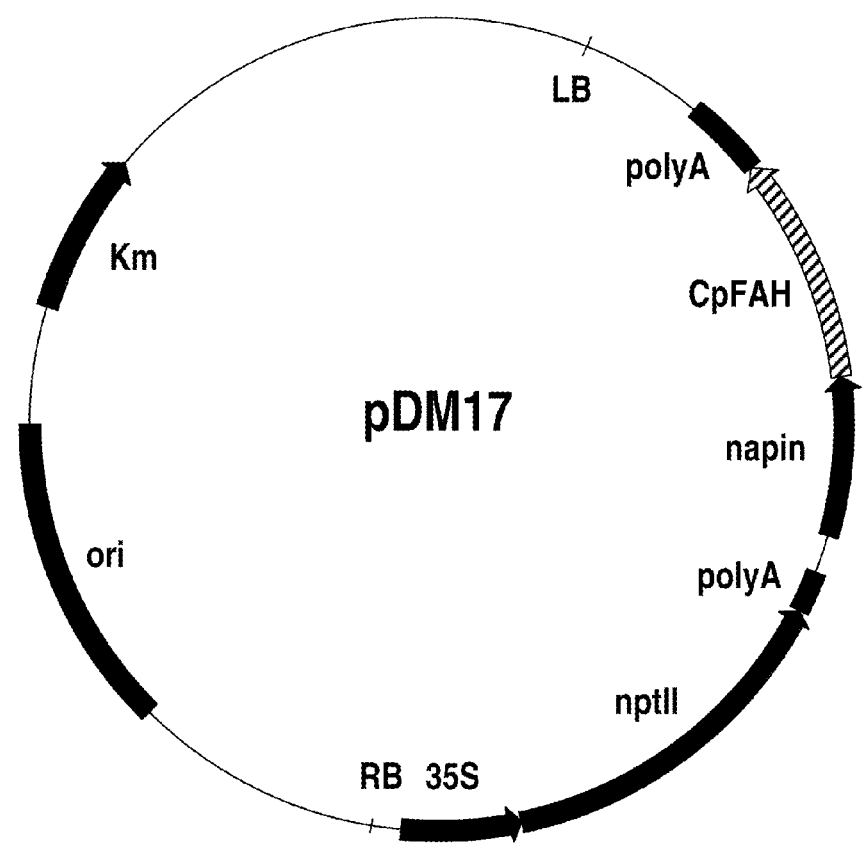
FIG. 5 is a depiction of an expression vector including CpFAH designed for large scale production of hydroxyl fatty acids in plants.

The present invention is based, at least in part, on the discovery of novel fatty acid hydroxylase family members, referred to interchangeably herein as "hydroxylases" or "hydroxylase" nucleic acid and protein molecules. These novel molecules are members of the fatty acid hydroxylase family and are expressed in the hydroxyl fatty acid-producing organisms *Claviceps purpurea* (*C. purpurea*). The present invention is further based, at least in part, on the discovery that the *C. purpurea* fatty acid hydroxylase (CpFAH) of the invention, and sufficiently homologous hydroxylases thereof, catalyze the introduction of a hydroxyl group in a fatty acid. The present invention is further based, at least in part, on the discovery that the *C. purpurea* fatty acid hydroxylase, and sufficiently homologous hydroxylases thereof, catalyze the introduction of a double bond, for example at position 12 of a fatty acid, such as oleic acid.

As used herein, the term "fatty acids" is art recognized and includes a long-chain hydrocarbon based carboxylic acid. Fatty acids are components of many lipids including glycerides. The most common naturally occurring fatty acids are monocarboxylic acids which have an even number of carbon atoms (16 or 18). Fatty acids may be hydroxylated or unhydroxylated. Hydroxylated fatty acids contain a hydroxyl group at least one position along the fatty acid chain.

The controlling steps in the production of hydroxyl fatty acids, i.e., the hydroxyl fatty acid biosynthetic pathway, are catalyzed by fatty acid hydroxylases, e.g., *C. purpurea* fatty acid hydroxylases (CpFAH). Specifically, such enzymes catalyze the formation of a hydroxyl group on a carbon atom of a fatty acid molecule. As used herein, the term "hydroxyl fatty acid biosynthetic pathway" refers to a series of chemical reactions leading to the synthesis of a hydroxyl fatty acid either in vivo or in vitro. Fatty acid hydroxylases such as CpFAH introduce a hydroxyl group into oleic acid (18:1-9) resulting in formation of ricinoleoc acid (12-OH-18:1-9).

The term "family" when referring to the protein and nucleic acid molecules of the present invention is intended to mean two or more proteins or nucleic acid molecules having a common structural domain or motif, for example, at least one of the conserved amino acid domains, GHECGH (SEQ ID NO: 6), HSAHH (SEQ ID NO: 7) and HVVHH (SEQ ID NO: 8), and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics. For example, the family of hydroxylase proteins of the present invention are involved in the introduction of a hydroxyl group, for example, in a fatty acid.

Figure 2:
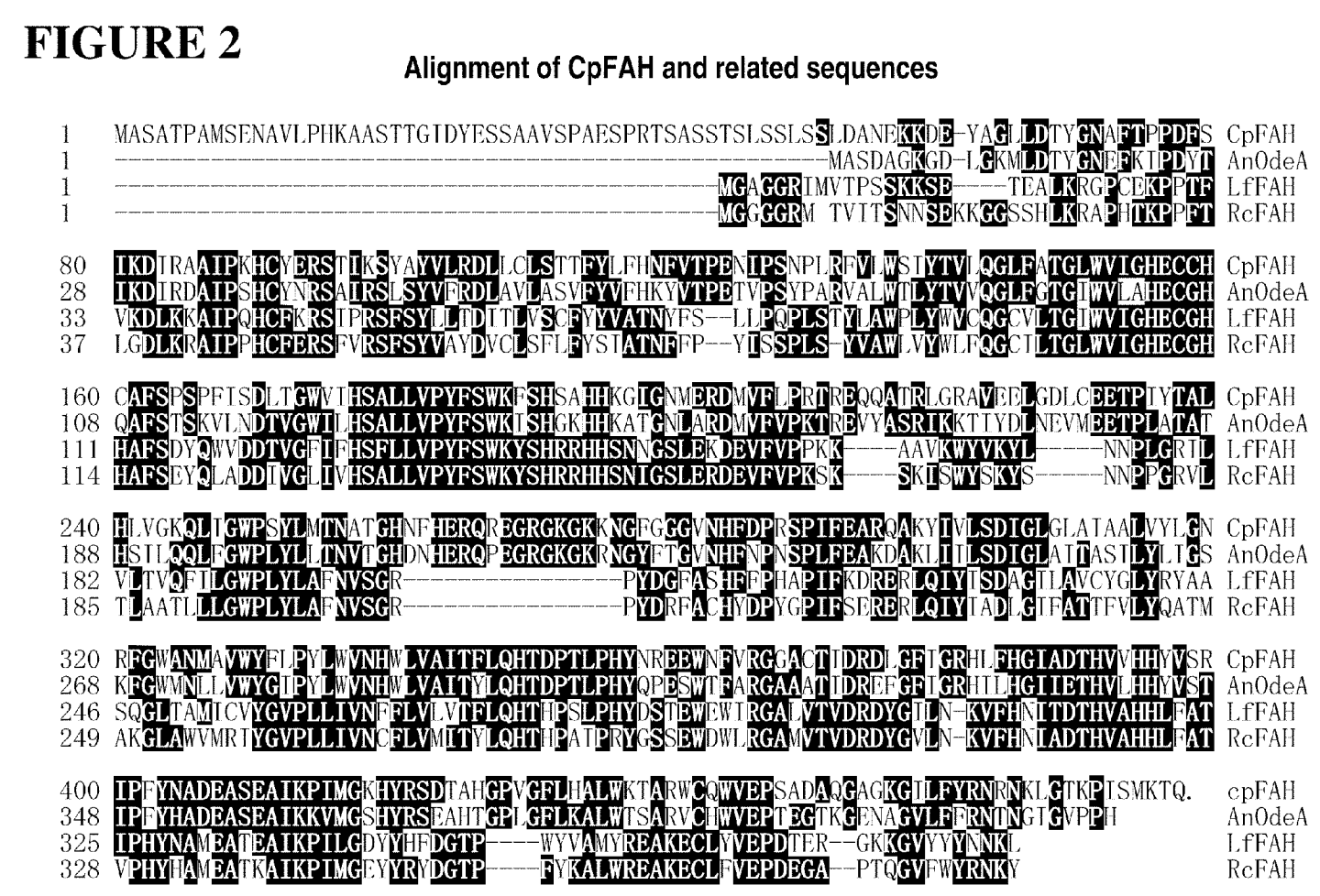

Isolated hydroxylase proteins of the present invention have an amino acid sequence sufficiently homologous to the amino acid sequence of SEQ ID NO:2 or are encoded by a nucleotide sequence sufficiently homologous to SEQ ID NO:1. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs, for example, those domains or motifs conserved among the various fatty acid hydroxylases depicted in FIG. 2, and/or a common functional activity. For example, amino acid or nucleotide sequences which share common structural domains having at least 50%, 55%, 60%, 65%, 70%, 75%, 80%, 85%, 90%, 95%, 96%, 97%, 98%, 99% or more homology or identity across the domains and contain at least one and preferably two structural domains or motifs, are defined herein as sufficiently homologous. Furthermore, amino acid or nucleotide sequences which share at least 50%, 55%, 60%, 65%, 70%, 75%, 80%, 85%, 90%, 95%, 96%, 97%, 98%, 99% or more homology or identity and share a common functional activity are defined herein as sufficiently homologous.

As used interchangeably herein, a "hydroxylase activity," "biological activity of a hydroxylase," or "functional activity of a hydroxylase," includes an activity exerted or mediated by a hydroxylase protein, polypeptide or nucleic acid molecule on a hydroxylase responsive cell or on a hydroxylase substrate, as determined in vivo or in vitro, according to standard techniques. In one embodiment, a hydroxylase activity is a direct activity such as an association with a hydroxylase target molecule. As used herein, a "target molecule" or "binding partner" is a molecule, for example, a molecule involved in the synthesis of hydroxyl fatty acids, e.g., an intermediate fatty acid (such as a hydroxylated fatty acid on which the incorporation of further hydroxyl groups is desired) or an unhydroxylated fatty acid, with which a hydroxylase protein binds or interacts in nature such that a hydroxylase-mediated function is achieved. In a particular embodiment, the target molecule or binding partner is octadec-9-enoic acid (oleic acid). A hydroxylase direct activity also includes the formation of a hydroxyl group on a fatty acid molecule to form a hydroxyl fatty acid molecule. For purposes of the present invention, the hydroxylase may introduce a hydroxyl group to an entirely unhydroxylated fatty acid or, alternatively, may introduce an additional hydroxyl group to a previously hydroxylated fatty acid.

The nucleotide sequence of the isolated *Claviceps purpurea* hydroxylase (CpFAH) cDNA and the predicted amino acid sequence encoded by the CpFAH cDNA are shown in FIG. 1. The *Claviceps purpurea* CpFAH gene (the open reading frame), which is approximately 1434 nucleotides in length, encodes a protein which is approximately 477 amino acid residues in length. The present invention is based, at least in part, on the discovery that the CpFAH molecule is a bifunctional enzyme with both hydroxylase and $\Delta^{12}$ desaturase activity. For example, the CpFAH molecule catalyzes the introduction of a hydroxyl group and/or a double bond in fatty acids, for example at position 12 of oleic acid.

As used herein, "oleic acid" refers to a monounsaturated omega-9 fatty acid found in various animal and vegetable sources. Oleic acid has the formula $C_{18}H_{34}O_2$ (or $CH_3(CH_2)_7 CH=CH(CH_2)_7COOH$) and is also known as cis-9-octadecenoic acid, octadec-9-enoic acid, 18:1-9 and 18:1 cis-9.

As used herein, "ricinoleic acid" refers to an unsaturated omega-9 fatty acid. Ricinoleic acid has the formula $C_{18}H_{34}O_3$ and is also known as 12-hydroxyoctadec-9-enoic acid.

Various aspects of the invention are described in further detail in the following subsections:

I. Isolated Nucleic Acid Molecules

One aspect of the invention pertains to isolated nucleic acid molecules that encode hydroxylase proteins or biologically active portions thereof, as well as nucleic acid fragments sufficient for use as hybridization probes to identify hydroxylase-encoding nucleic acid molecules (e.g., hydroxylase mRNA) and fragments for use as PCR primers for the amplification or mutation of hydroxylase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated hydroxylase nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, or a portion thereof, can be isolated using standard molecular biology techniques and the sequence information provided herein. Using all or a portion of the nucleic acid sequence of SEQ ID NO:1, as hybridization probes, hydroxylase nucleic acid molecules can be isolated using standard hybridization and cloning techniques (e.g., as described in Sambrook, J. et al. *Molecular Cloning: A Laboratory Manual.* $2^{nd}$, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, can be isolated by the polymerase chain reaction (PCR) using synthetic oligonucleotide primers designed based upon the sequence of SEQ ID NO:1.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to hydroxylase nucleotide sequences can be prepared by standard synthetic techniques, e.g., using an automated DNA synthesizer.

In still another embodiment, an isolated nucleic acid molecule of the invention includes the complement of the nucleotide sequence shown in SEQ ID NO: 1, or a portion thereof. A nucleic acid molecule which is complementary to the nucleotide sequence shown in SEQ ID NO:1 is one which is sufficiently complementary to the nucleotide sequence shown in SEQ ID NO:1, such that it can hybridize to the nucleotide sequence shown in SEQ ID NO:1, thereby forming a stable duplex. In a particular embodiment, the complementary sequences of the invention are exact complements of the nucleic acid molecules of the invention, for example, a nucleotide sequence of SEQ ID NO:1, a nucleotide sequence encoding a polypeptide of SEQ ID NO:2, or an allelic variant thereof, and a nucleotide sequence of at least 70% identity to the nucleotide sequence of SEQ ID NO:1. For example, the complement may be a full and complete complement of a nucleic acid molecule of the invention, for example, the nucleotide sequence of SEQ ID NO:1.

In still another embodiment, an isolated nucleic acid molecule of the invention comprises a nucleotide sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, 91%, 92%, 93%, 94%, and even more preferably at least about 95%, 96%, 97%, 98%, 99% or more identical to the nucleotide sequence of SEQ ID NO:1 (e.g., to the entire nucleotide sequence of SEQ ID NO:1), or a portion or a complement thereof. Ranges and identity values intermediate to the above-recited ranges, (e.g., 70-90% identical or 80-95% identical) are also intended to be encompassed by the present invention. For example, ranges of identity values using a combination of any of the above values recited as upper and/or lower limits are intended to be included.

In one embodiment, a nucleic acid molecule of the present invention comprises a nucleotide sequence which is at least (or no greater than) 50, 100, 150, 200, 250, 300, 350, 400, 450, 500, 550, 600, 650, 700, 750, 1000 or 1250 or more nucleotides in length and hybridizes under stringent hybridization conditions to a complement of a nucleic acid molecule of SEQ ID NO:1.

Moreover, the nucleic acid molecule of the invention can comprise only a portion of the nucleic acid sequence of SEQ ID NO:1, for example, a fragment which can be used as a probe or primer or a fragment encoding a portion of a hydroxylase protein, e.g., a biologically active portion of a hydroxylase protein. The nucleotide sequence determined from the cloning of the hydroxylase gene allows for the generation of probes and primers designed for use in identifying and/or cloning other hydroxylase family members, as well as hydroxylase homologues from other species. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, of an anti-sense sequence of SEQ ID NO: 1, or of a naturally occurring allelic variant or mutant of SEQ ID NO: 1.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the hydroxylase nucleotide sequences can be used to detect (e.g., specifically detect) transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. In another embodiment, a set of primers is provided, e.g., primers suitable for use in a PCR, which can be used to amplify a selected region of a hydroxylase sequence, e.g., a domain, region, site or other sequence described herein. The primers should be at least 5, 10, 15, 20, 25, 30, 35, 40, 45 or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress a hydroxylase protein, such as by measuring a level of a hydroxylase-encoding nucleic acid in a sample of cells from a subject, e.g., detecting hydroxylase mRNA levels or determining whether a genomic hydroxylase gene has been mutated or deleted.

A nucleic acid fragment encoding a "biologically active portion of a hydroxylase protein" can be prepared by isolating a portion of the nucleotide sequence of SEQ ID NO: 1, which encodes a polypeptide having a hydroxylase biological activity (the biological activities of the hydroxylase proteins are described herein), expressing the encoded portion of the hydroxylase protein (e.g., by recombinant expression in vitro) and assessing the activity of the encoded portion of the hydroxylase protein using standard assay techniques known in the art or those techniques described, for example, in the Examples set forth herein. In an exemplary embodiment, the nucleic acid molecule is at least 50, 100, 150, 200, 250, 300, 350, 400, 450, 500, 550, 600, 650, 700, 750, 1000 or 1250 or more nucleotides in length and encodes a protein having a hydroxylase activity (as described herein).

The invention further encompasses nucleic acid molecules that differ from the nucleotide sequence shown in SEQ ID NO:1 due to degeneracy of the genetic code and thus encode the same hydroxylase proteins as those encoded by the nucleotide sequence shown in SEQ ID NO:1. In another embodiment, an isolated nucleic acid molecule of the invention has a nucleotide sequence encoding a protein having an amino acid sequence which differs by at least 1, but no greater than 5, 10, 20, 50 or 100 amino acid residues from the amino acid sequence shown in SEQ ID NO:2. In yet another embodiment, the nucleic acid molecule encodes the amino acid sequence of human hydroxylase. If an alignment is needed for this comparison, the sequences should be aligned for maximum homology.

Nucleic acid variants can be naturally occurring, such as allelic variants (same locus), homologues (different locus), and orthologues (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the hydroxylase proteins. Such genetic polymorphism in the hydroxylase genes may exist among individuals within a population due to natural allelic variation.

As used herein, the terms "gene" and "recombinant gene" refer to nucleic acid molecules which include an open reading frame encoding a hydroxylase protein, e.g., oilseed hydroxylase protein, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:2. Moreover, the nucleic acid molecule may hybridize to a complement of a nucleic acid molecule comprising SEQ ID NO:1, for example, under stringent hybridization conditions.

In addition to the *C. purpurea* fatty acid hydroxylase of SEQ ID NO: 1, it will be appreciated by those of ordinary skill in the art that DNA sequence polymorphisms that lead to changes in the amino acid sequences of the hydroxylase proteins may exist within a population (e.g., the *C. purpurea* population). Such genetic polymorphism in the fatty acid hydroxylase gene may exist among individuals within a population due to natural variation. Such natural variations can typically result in 1-5% variance in the nucleotide sequence of the HA gene. Allelic variants of the CpFAH hydroxylase include both functional and non-functional hydroxylase proteins. Functional allelic variants are naturally occurring amino acid sequence variants of the hydroxylase protein that maintain the ability to, e.g., (i) interact with a hydroxylase substrate or target molecule (e.g., a fatty acid); and/or (ii) form a hydroxyl group in a hydroxylase substrate or target molecule. Functional allelic variants will typically contain only a conservative substitution of one or more amino acids of SEQ ID NO:2, or a substitution, deletion or insertion of non-critical residues in non-critical regions of the protein.

Non-functional allelic variants are naturally occurring amino acid sequence variants of the hydroxylase protein that do not have the ability to, e.g., (i) interact with a hydroxylase substrate or target molecule (e.g., a fatty acid such as an unhydroxylated fatty acid); and/or (ii) form a hydroxyl group in a hydroxylase substrate or target molecule. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

The present invention further provides orthologues (e.g., human orthologues of the hydroxylase proteins). Orthologues of the *C. purpurea* hydroxylase proteins are proteins that are isolated from other organisms and possess the same hydroxylase substrate or target molecule binding mechanisms and/or hydroxyl group forming mechanisms. Orthologues of the *C. purpurea* hydroxylase proteins can readily be identified as comprising an amino acid sequence that is substantially homologous to SEQ ID NO:2.

Moreover, nucleic acid molecules encoding other hydroxylase family members and, thus, which have a nucleotide sequence which differs from the hydroxylase sequences of SEQ ID NO:1 are intended to be within the scope of the invention. For example, another hydroxylase cDNA can be identified based on the nucleotide sequence of SEQ ID NO:1. Moreover, nucleic acid molecules encoding hydroxylase proteins from different species, and which, thus, have a nucleotide sequence which differs from the hydroxylase sequences of SEQ ID NO:1, are intended to be within the scope of the invention. For example, *Schizochytrium* or *Crythecodinium* hydroxylase cDNA can be identified based on the nucleotide sequence of a *C. purpurea* fatty acid hydroxylase.

Nucleic acid molecules corresponding to natural allelic variants and homologues of the hydroxylase cDNAs of the invention can be isolated based on their homology to the hydroxylase nucleic acids disclosed herein using the cDNAs disclosed herein, or a portion thereof, as a hybridization probe according to standard hybridization techniques under stringent hybridization conditions.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or a complement of the nucleotide sequence of SEQ ID NO:1, for example, the exact complement of the nucleotide sequence of SEQ ID NO:1. In other embodiment, the nucleic acid is at least 50, 100, 150, 200, 250, 300, 350, 400, 450, 500, 550, 600, 650, 700, 750, 1000 or 1250 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$ (°C.)=$81.5+16.6(\log_{10}[Na^+])+0.41(\%G+C)-(600/N)$, where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including, but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (see e.g., Church and Gilbert (1984) *Proc. Natl. Acad. Sci. USA* 81:1991-1995), or alternatively 0.2×SSC, 1% SDS.

Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the hydroxylase sequences that may exist in the population, the skilled artisan will further appreciate that changes can be introduced by mutation into the nucleotide sequences of SEQ ID NO:1, thereby leading to changes in the amino acid sequence of the encoded hydroxylase proteins, without altering the functional ability of the hydroxylase proteins. For example, nucleotide substitutions leading to amino acid substitutions at "non-essential" amino acid residues can be made in the sequence of SEQ ID NO:1. A "non-essential" amino acid residue is a residue that can be altered from the wild-type sequence of *C. purpurea* fatty acid hydroxylase (e.g., the sequence of SEQ ID NO:2) without altering the biological activity, whereas an "essential" amino acid residue is required for biological activity. For example, amino acid residues that are conserved between the hydroxylase proteins of the present invention and other members of the fatty acid hydroxylase family are not likely to be amenable to alteration.

Accordingly, another aspect of the invention pertains to nucleic acid molecules encoding hydroxylase proteins that contain changes in amino acid residues that are not essential for activity. Such hydroxylase proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99% or more identical to SEQ ID NO:2, e.g., to the entire length of SEQ ID NO:2.

An isolated nucleic acid molecule encoding a hydroxylase protein homologous to the protein of SEQ ID NO:2 can be created by introducing one or more nucleotide substitutions, additions or deletions into the nucleotide sequence of SEQ ID NO:1, such that one or more amino acid substitutions, additions or deletions are introduced into the encoded protein. Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a hydroxylase protein is preferably replaced with another amino acid residue from the same side chain family. Alternatively, in another embodiment, mutations can be introduced randomly along all or part of a hydroxylase coding sequence, such as by saturation mutagenesis, and the resultant mutants can be screened for hydroxylase biological activity to identify mutants that retain activity. Following mutagenesis of SEQ ID NO:1, the encoded protein can be expressed recombinantly and the activity of the protein can be determined.

In a preferred embodiment, a mutant hydroxylase protein can be assayed for the ability to (i) interact with a hydroxylase substrate or target molecule (e.g., a fatty acid) and/or (ii) form a hydroxyl group in a hydroxylase substrate or target molecule using standard assays known in the art or those assays described herein, for example, in the Examples.

II. Isolated Hydroxylase Proteins

One aspect of the invention pertains to isolated or recombinant hydroxylase proteins and polypeptides, and biologically active portions thereof. In one embodiment, native hydroxylase proteins can be isolated from cells or tissue sources by an appropriate purification scheme using standard protein purification techniques. In another embodiment, hydroxylase proteins are produced by recombinant DNA techniques. Alternative to recombinant expression, a hydroxylase protein or polypeptide can be synthesized chemically using standard peptide synthesis techniques.

An "isolated" or "purified" protein or biologically active portion thereof is substantially free of cellular material or other contaminating proteins from the cell or tissue source from which the hydroxylase protein is derived, or substantially free from chemical precursors or other chemicals when chemically synthesized. The language "substantially free of cellular material" includes preparations of hydroxylase protein in which the protein is separated from cellular components of the cells from which it is isolated or recombinantly produced. In one embodiment, the language "substantially free of cellular material" includes preparations of hydroxylase protein having less than about 80%, 70%, 60%, 50%, 40%, or 30% (by dry weight) of non-hydroxylase protein (also referred to herein as a "contaminating protein"), more preferably less than about 20% of non-hydroxylase protein, still more preferably less than about 10% of non-hydroxylase protein, and most preferably less than about 5% non-hydroxylase protein. When the hydroxylase protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of hydroxylase protein in which the protein is separated from chemical precursors or other chemicals which are involved in the synthesis of the protein. In one embodiment, the language "substantially free of chemical precursors or other chemicals" includes preparations of hydroxylase protein having less than about 30% (by dry weight) of chemical precursors or non-hydroxylase chemicals, more preferably less than about 20% chemical precursors or non-hydroxylase chemicals, still more preferably less than about 10% chemical precursors or non-hydroxylase chemicals, and most preferably less than about 5% chemical precursors or non-hydroxylase chemicals. It should be understood that the proteins of this invention can also be in a form which is different than their corresponding naturally occurring proteins and/or which is still in association with at least some cellular components. For example, the protein can be associated with a cellular membrane.

As used herein, a "biologically active portion" of a hydroxylase protein includes a fragment of a hydroxylase protein which participates in an interaction between a hydroxylase molecule and a non-hydroxylase molecule (e.g., a hydroxylase substrate such as fatty acid). Biologically active portions of a hydroxylase protein include peptides comprising amino acid sequences sufficiently homologous to or derived from the hydroxylase amino acid sequences, e.g., the amino acid sequences shown in SEQ ID NO:2 which include sufficient amino acid residues to exhibit at least one activity of a hydroxylase protein. Typically, biologically active portions comprise a domain or motif with at least one activity of the hydroxylase protein, for example, the ability to (i) interact with a hydroxylase substrate or target molecule (e.g., a fatty acid) and/or (ii) form a hydroxyl group in a hydroxylase substrate or target molecule, A biologically active portion of a hydroxylase protein can be a polypeptide which is, for example, 10, 15, 20, 25, 30, 35, 40, 45, 50, 75, 100, 125, 150, 175, 200, 250, 300, 350, 400 or 450 or more amino acids in length.

In one embodiment, a biologically active portion of a hydroxylase protein comprises a domain conserved among hydroxylases and known to participate in a hydroxylase activity. For example, at least one domain or motif conserved among at least two, at least three or the four amino acid sequences encoding fatty acid hydroxylases from different organisms, as depicted in FIG. 2, can be incorporated within the biologically active fragments in order to preserve hydroxylase activity. Specifically, hydroxylases often possess the following conserved amino acid domains: GHECGH (SEQ ID NO: 6), HSAHH (SEQ ID NO: 7) and HVVHH (SEQ ID NO: 8). Accordingly, in particular embodiments of the present invention, biologically active fragments of polypeptides include at least one domain selected from the group consisting of GHECGH (SEQ ID NO: 6), HSAHH (SEQ ID NO: 7) and HVVHH (SEQ ID NO: 8). In other embodiments, nucleic acid molecules encoding for biologically active fragments include nucleotide sequences encoding for at least one domain selected from the group consisting of GHECGH (SEQ ID NO: 6), HSAHH (SEQ ID NO: 7) and HVVHH (SEQ ID NO: 8). Moreover, other biologically active portions, in which other regions of the protein are deleted, can be prepared by recombinant techniques and evaluated for one or more of the functional activities of a native hydroxylase protein.

In a preferred embodiment, a hydroxylase protein has an amino acid sequence shown in SEQ ID NO:2. In other embodiments, the hydroxylase protein is substantially identical to SEQ ID NO:2 and retains the functional activity of the protein of SEQ ID NO:2, yet differs in amino acid sequence due to natural allelic variation or mutagenesis, as described in detail in subsection I above. In another embodiment, the hydroxylase protein is a protein which comprises an amino acid sequence at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, 91%, 92%, 93%, 94%, and even more preferably at least about 95%, 96%, 97%, 98%, 99% or more identical to SEQ ID NO:2.

In another embodiment, the invention features a hydroxylase protein which is encoded by a nucleic acid molecule consisting of a nucleotide sequence at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, 91%, 92%, 93%, 94%, and even more preferably at least about 95%, 96%, 97%, 98%, 99% or more identical to a nucleotide sequence of SEQ ID NO:1, or a complement thereof. This invention further features a hydroxylase protein which is encoded by a nucleic acid molecule consisting of a nucleotide sequence which hybridizes under stringent hybridization conditions to a complement of a nucleic acid molecule comprising the nucleotide sequence of SEQ ID NO:1.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the *C. purpurea* fatty acid hydroxylase amino acid sequence of SEQ ID NO:2 having 477 amino acid residues, at least 143, preferably at least 191, more preferably at least 238, even more preferably at least 286, and even more preferably at least 334, 382, or 429 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (*Comput. Appl. Biosci.*, 4:11-17 (1988)) which has been incorporated into the ALIGN program (version 2.0 or version 2.0U), using a PAM 120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to hydroxylase nucleic acid molecules of the invention. BLAST protein searches can be performed with the XBLAST program, score=50, wordlength=3 to obtain amino acid sequences homologous to hydroxylase protein molecules of the invention. To obtain gapped alignments for comparison purposes, Gapped BLAST can be utilized as described in Altschul et al. (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

III. Methods of Producing Hydroxyl Fatty Acids

The present invention provides new and improved methods of producing hydroxyl fatty acids, e.g., 12-hydroxyoctadec-9-enoic acid (ricinoleic acid) or lesqueroileic acid.

A. Recombinant Cells and Methods for Culturing Cells

The present invention further features recombinant vectors that include nucleic acid sequences that encode the gene products as described herein, preferably hydroxylase gene products. The term recombinant vector includes a vector (e.g., plasmid) that has been altered, modified or engineered such that it contains greater, fewer or different nucleic acid sequences than those included in the native vector or plasmid. In one embodiment, a recombinant vector includes the nucleic acid sequence encoding at least one fatty acid hydroxylase enzyme operably linked to regulatory sequences. The phrase "operably linked to regulatory sequence(s)" means that the nucleotide sequence of interest is linked to the regulatory sequence(s) in a manner which allows for expression (e.g., enhanced, increased, constitutive, basal, attenuated, decreased or repressed expression) of the nucleotide sequence, preferably expression of a gene product encoded by the nucleotide sequence (e.g., when the recombinant vector is introduced into a cell). Exemplary vectors are described in further detail herein as well as in, for example, Frascotti et al., U.S. Pat. No. 5,721,137, the contents of which are incorporated herein by reference.

The term "regulatory sequence" includes nucleic acid sequences which affect (e.g., modulate or regulate) expression of other (non-regulatory) nucleic acid sequences. In one embodiment, a regulatory sequence is included in a recombinant vector in a similar or identical position and/or orientation relative to a particular gene of interest as is observed for the regulatory sequence and gene of interest as it appears in nature, e.g., in a native position and/or orientation. For example, a gene of interest (e.g., a *C. purpurea* fatty acid hydroxylase gene) can be included in a recombinant vector operably linked to a regulatory sequence which accompanies or is adjacent to the gene in the natural organism (e.g., operably linked to "native" fatty acid regulatory sequence such as the "native" fatty acid hydroxylase promoter). Alternatively, a gene of interest (e.g., a fatty acid hydroxylase gene) can be included in a recombinant vector operably linked to a regulatory sequence which accompanies or is adjacent to another (e.g., a different) gene in the natural organism. For example, a fatty acid hydroxylase gene can be included in a vector operably linked to non-fatty acid hydroxylase regulatory sequences. Alternatively, a gene of interest (e.g., a fatty acid hydroxylase gene) can be included in a vector operably linked to a regulatory sequence from another organism. For example, regulatory sequences from other microbes (e.g., other bacterial regulatory sequences, bacteriophage regulatory sequences and the like) can be operably linked to a particular gene of interest.

Preferred regulatory sequences include promoters, enhancers, termination signals and other expression control elements (e.g., binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. Regulatory sequences include those which direct constitutive expression of a nucleotide sequence in a cell (e.g., constitutive promoters and strong constitutive promoters), those which direct inducible expression of a nucleotide sequence in a cell (e.g., inducible promoters, for example, xylose inducible promoters) and those which attenuate or repress expression of a nucleotide sequence in a cell (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant vector of the present invention includes nucleic acid sequences that encode at least one gene product (e.g., *C. purpurea* fatty acid hydroxylase) operably linked to a promoter or promoter sequence.

In a particular embodiment, seed-specific promoters are utilized to enhance the production of the desired hydroxyl fatty acid. For example, U.S. Patent Publication No. 2003-0159174, published Aug. 21, 2003, the entire contents of which are hereby expressly incorporated by reference herein, describes the use of particular seed-specific promoters including, for example, Conlinin 1, Conlinin 2 and LuFad3 from the genus *Linum*. One skilled in the art will appreciate that other promoters, for example, seed specific promoters such as napin, may be utilized to modulate, for example, enhance, the expression of the hydroxylase nucleotide sequence.

In yet another embodiment, a recombinant vector of the present invention includes a terminator sequence or terminator sequences (e.g., transcription terminator sequences). The term "terminator sequences" includes regulatory sequences which serve to terminate transcription of mRNA. Terminator sequences (or tandem transcription terminators) can further serve to stabilize mRNA (e.g., by adding structure to mRNA), for example, against nucleases.

In yet another embodiment, a recombinant vector of the present invention includes antibiotic resistance sequences. The term "antibiotic resistance sequences" includes sequences which promote or confer resistance to antibiotics on the host organism. In one embodiment, the antibiotic resistance sequences are selected from the group consisting of cat (chloramphenicol resistance), tet (tetracycline resistance) sequences, erm (erythromycin resistance) sequences, neo (neomycin resistance) sequences and spec (spectinomycin resistance) sequences. Recombinant vectors of the present invention can further include homologous recombination sequences (e.g., sequences designed to allow recombination of the gene of interest into the chromosome of the host organism). For example, amyE sequences can be used as homology targets for recombination into the host chromosome.

The term "manipulated cell" includes a cell that has been engineered (e.g., genetically engineered) or modified such that the cell has at least one fatty acid hydroxylase of the invention (e.g., SEQ ID NO:1), such that a hydroxyl fatty acid is produced. Modification or engineering of such microorganisms can be according to any methodology described herein including, but not limited to, deregulation of a biosynthetic pathway and/or overexpression of at least one biosynthetic enzyme. A "manipulated" enzyme (e.g., a "manipulated" biosynthetic enzyme) includes an enzyme, the expression or production of which has been altered or modified such that at least one upstream or downstream precursor, substrate or product of the enzyme is altered or modified, for example, as compared to a corresponding wild-type or naturally occurring enzyme.

The term "overexpressed" or "overexpression" includes expression of a gene product (e.g., a fatty acid hydroxylase) at a level greater than that expressed prior to manipulation of the cell or in a comparable cell which has not been manipulated. In one embodiment, the cell can be genetically manipulated (e.g., genetically engineered) to overexpress a level of gene product greater than that expressed prior to manipulation of the cell or in a comparable cell which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins).

In another embodiment, the cell can be physically or environmentally manipulated to overexpress a level of gene product greater than that expressed prior to manipulation of the cell or in a comparable cell which has not been manipulated. For example, a cell can be treated with or cultured in the presence of an agent known or suspected to increase transcription of a particular gene and/or translation of a particular gene product such that transcription and/or translation are enhanced or increased. Alternatively, a cell can be cultured at a temperature selected to increase transcription of a particular gene and/or translation of a particular gene product such that transcription and/or translation are enhanced or increased.

The term "deregulated" or "deregulation" includes the alteration or modification of at least one gene in a cell that encodes an enzyme in a biosynthetic pathway, such that the level or activity of the biosynthetic enzyme in the cell is altered or modified. Preferably, at least one gene that encodes an enzyme in a biosynthetic pathway is altered or modified such that the gene product is enhanced or increased. The phrase "deregulated pathway" can also include a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene in a given biosynthetic pathway) in a cell arises from the particular phenomenon of cells in which more than one enzyme (e.g., two or three biosynthetic enzymes) are encoded by genes occurring adjacent to one another on a contiguous piece of genetic material termed an "operon".

The term "operon" includes a coordinated unit of gene expression that contains a promoter and possibly a regulatory element associated with one or more, preferably at least two, structural genes (e.g., genes encoding enzymes, for example, biosynthetic enzymes). Expression of the structural genes can be coordinately regulated, for example, by regulatory proteins binding to the regulatory element or by anti-termination of transcription. The structural genes can be transcribed to give a single mRNA that encodes all of the structural proteins. Due to the coordinated regulation of genes included in an operon, alteration or modification of the single promoter and/or regulatory element can result in alteration or modification of each gene product encoded by the operon. Alteration or modification of the regulatory element can include, but is not limited to removing the endogenous promoter and/or regulatory element(s), adding strong promoters, inducible promoters or multiple promoters or removing regulatory sequences such that expression of the gene products is modified, modifying the chromosomal location of the operon, altering nucleic acid sequences adjacent to the operon or within the operon such as a ribosome binding site, increasing the copy number of the operon, modifying proteins (e.g., regulatory proteins, suppressors, enhancers, transcriptional activators and the like) involved in transcription of the operon and/or translation of the gene products of the operon, or any other conventional means of deregulating expression of genes routine in the art (including but not limited to use of antisense nucleic acid molecules, for example, to block expression of repressor proteins). Deregulation can also involve altering the coding region of one or more genes to yield, for example, an enzyme that is feedback resistant or has a higher or lower specific activity.

A particularly preferred "recombinant" cell of the present invention has been genetically engineered to overexpress a plant-derived gene or gene product or an microorganismally-derived gene or gene product. The term "plant-derived," "microorganismally-derived," or "derived-from," for example, includes a gene which is naturally found in a microorganism or a plant, e.g., an oilseed plant, or a gene product (e.g., the fatty acid hydroxylase of SEQ ID NO:2) or which is encoded by a plant gene or a gene from a microorganism (e.g., encoded SEQ ID NO:1).

The methodologies of the present invention feature recombinant cells which overexpress at least one fatty acid hydroxylase. In one embodiment, a recombinant cell of the present invention has been genetically engineered to overexpress a *Claviceps* fatty acid hydroxylase (e.g., a fatty acid hydroxylase having the amino acid sequence of SEQ ID NO:2 or encoded by the nucleic acid sequence of SEQ ID NO:1).

In another embodiment, the invention features a cell (e.g., a plant or microbial cell) that has been transformed with a vector comprising a fatty acid hydroxylase nucleic acid sequence (e.g., a fatty acid hydroxylase nucleic acid sequence as set forth in SEQ ID NO:1).

Another aspect of the present invention features a method of modulating the production of hydroxyl fatty acids comprising culturing cells transformed by the nucleic acid molecules of the present invention (e.g., a hydroxylase) such that modulation of hydroxyl fatty acid production occurs (e.g., production of hydroxyl fatty acids is enhanced). The method of culturing cells transformed by the nucleic acid molecules of the present invention to modulate the production of fatty acids is referred to herein as "biotransformation." The biotransformation processes can utilize recombinant cells and/or hydroxylases described herein. The term "biotransformation process," also referred to herein as "bioconversion processes," includes biological processes which result in the production (e.g., transformation or conversion) of any compound (e.g., substrate, intermediate, or product) which is upstream of a fatty acid hydroxylase to a compound (e.g., substrate, intermediate, or product) which is downstream of a fatty acid hydroxylase, in particular, a hydroxyl fatty acid. In one embodiment, the invention features a biotransformation process for the production of a hydroxyl fatty acid comprising contacting a cell which overexpresses at least one fatty acid hydroxylase with at least one appropriate substrate, for example, an unhydroxylated fatty acid, under conditions such that a hydroxyl fatty acid is produced and, optionally, recovering the fatty acid. In a preferred embodiment, the invention features a biotransformation process for the production of hydroxyl fatty acids comprising contacting a cell which overexpresses a fatty acid hydroxylase with an appropriate substrate (e.g., an intermediate fatty acid) under conditions such that a hydroxyl fatty acid (e.g., ricinoleic and lesqueroleic acid) is produced and, optionally, recovering the hydroxyl fatty acid. Conditions under which a hydroxyl fatty acid is produced can include any conditions which result in the desired production of a hydroxyl fatty acid.

The cell(s) and/or enzymes used in the biotransformation reactions are in a form allowing them to perform their intended function (e.g., producing a desired hydroxyl fatty acid). The cells can be whole cells, or can be only those portions of the cells necessary to obtain the desired end result. The cells can be suspended (e.g., in an appropriate solution such as buffered solutions or media), rinsed (e.g., rinsed free of media from culturing the cell), acetone-dried, immobilized (e.g., with polyacrylamide gel or k-carrageenan or on synthetic supports, for example, beads, matrices and the like), fixed, cross-linked or permeablized (e.g., have permeablized membranes and/or walls such that compounds, for example, substrates, intermediates or products can more easily pass through said membrane or wall).

The type of cell can be any cell capable of being used within the methods of the invention, e.g., plant, animal, or microbial cells, preferably a plant or microbial cell. In one embodiment, the cell is a plant cell, for example, an oilseed plant, including, but not limited to, flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla. In another embodiment, the cell is *Brassica juncea*. U.S. Patent Publication No. 2003-0159174, published Aug. 21, 2003, the entire contents of which are hereby expressly incorporated by reference herein, provides extensive teaching on the transformation of plant cells to optimize production of a desired end product.

In yet another embodiment, the cell is a microbial cell, for example, *Candida, Cryptococcus, Lipomyces, Rhodospo-*

*ridium, Yarrowia, Thraustochytrium, Pythium irregulare, Schizochytrium* and *Cythecodinium*. One skilled in the art will appreciate that other microbial cells can be used in accordance with the methods provided herein, for example, for the production of a hydroxyl fatty acid.

An important aspect of the present invention involves growing the recombinant plant or culturing the recombinant microorganisms described herein, such that a desired compound (e.g., a desired hydroxyl fatty acid) is produced. The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid media) comprising nutrients essential or beneficial to the maintenance and/or growth of the microorganism (e.g., carbon sources or carbon substrate, for example complex carbohydrates such as bean or grain meal, starches, sugars, sugar alcohols, hydrocarbons, oils, fats, fatty acids, organic acids and alcohols; nitrogen sources, for example, vegetable proteins, peptones, peptides and amino acids derived from grains, beans and tubers, proteins, peptides and amino acids derived form animal sources such as meat, milk and animal byproducts such as peptones, meat extracts and casein hydrolysates; inorganic nitrogen sources such as urea, ammonium sulfate, ammonium chloride, ammonium nitrate and ammonium phosphate; phosphorus sources, for example, phosphoric acid, sodium and potassium salts thereof; trace elements, for example, magnesium, iron, manganese, calcium, copper, zinc, boron, molybdenum, and/or cobalt salts; as well as growth factors such as amino acids, vitamins, growth promoters and the like).

Preferably, microorganisms of the present invention are cultured under controlled pH. The term "controlled pH" includes any pH which results in production of the desired product (e.g., a hydroxyl fatty acid). In one embodiment, microorganisms are cultured at a pH of about 7. In another embodiment, microorganisms are cultured at a pH of between 6.0 and 8.5. The desired pH may be maintained by any number of methods known to those skilled in the art.

Also preferably, microorganisms of the present invention are cultured under controlled aeration. The term "controlled aeration" includes sufficient aeration (e.g., oxygen) to result in production of the desired product (e.g., a hydroxyl fatty acid). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the growth vessel (e.g., fermentor) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents).

Moreover, plants or microorganisms of the present invention can be cultured under controlled temperatures. The term "controlled temperature" includes any temperature which results in production of the desired product (e.g., a hydroxyl fatty acid). In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 45° C. or between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous methods of fermentation. The phrase "batch process" or "batch fermentation" refers to a closed system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired product (e.g., a hydroxyl fatty acid). A variety of such processes have been developed and are well-known in the art.

The phrase "culturing under conditions such that a desired compound is produced" includes maintaining and/or growing plants or microorganisms under conditions (e.g., temperature, pressure, pH, duration, etc.) appropriate or sufficient to obtain production of the desired compound or to obtain desired yields of the particular compound being produced, for example, a hydroxyl fatty acid such as ricinoleic or lesqueroleic acid. For example, culturing is continued for a time sufficient to produce the desired amount of a hydroxyl fatty acid. Preferably, culturing is continued for a time sufficient to substantially reach maximal production of the hydroxyl fatty acid. In one embodiment, culturing is continued for about 12 to 24 hours. In another embodiment, culturing is continued for about 24 to 36 hours, 36 to 48 hours, 48 to 72 hours, 72 to 96 hours, 96 to 120 hours, 120 to 144 hours, or greater than 144 hours. In another embodiment, culturing is continued for a time sufficient to reach production yields of hydroxyl fatty acids, for example, cells are cultured such that at least about 15 to 20 g/L of hydroxyl fatty acids are produced, at least about 20 to 25 g/L hydroxyl fatty acids are produced, at least about 25 to 30 g/L hydroxyl fatty acids are produced, at least about 30 to 35 g/L hydroxyl fatty acids are produced, at least about 35 to 40 g/L hydroxyl fatty acids are produced (e.g., at least about 37 g/L hydroxyl fatty acids) or at least about 40 to 50 g/L hydroxyl fatty acids are produced. In yet another embodiment, microorganisms are cultured under conditions such that a preferred yield of hydroxyl fatty acids, for example, a yield within a range set forth above, is produced in about 24 hours, in about 36 hours, in about 48 hours, in about 72 hours, or in about 96 hours.

In producing hydroxyl fatty acids, it may further be desirable to culture cells of the present invention in the presence of supplemental fatty acid biosynthetic substrates. The term "supplemental fatty acid biosynthetic substrate" includes an agent or compound which, when brought into contact with a cell or included in the culture medium of a cell, serves to enhance or increase hydroxyl fatty acid biosynthesis. Supplemental fatty acid biosynthetic substrates of the present invention can be added in the form of a concentrated solution or suspension (e.g., in a suitable solvent such as water or buffer) or in the form of a solid (e.g., in the form of a powder). Moreover, supplemental fatty acid biosynthetic substrates of the present invention can be added as a single aliquot, continuously or intermittently over a given period of time.

The methodology of the present invention can further include a step of recovering a desired compound (e.g., a hydroxyl fatty acid). The term "recovering" a desired compound includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a compound can be recovered from culture media by first removing the microorganisms from the culture. Media is then passed through or over a cation exchange resin to remove unwanted cations and then through or over an anion exchange resin to remove unwanted inorganic anions and organic acids having stronger acidities than the hydroxyl fatty acid of interest (e.g., ricinoleic acid).

Preferably, a desired compound of the present invention is "extracted," "isolated" or "purified" such that the resulting preparation is substantially free of other components (e.g., free of media components and/or fermentation byproducts). The language "substantially free of other components" includes preparations of desired compound in which the compound is separated (e.g., purified or partially purified) from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98-99% desired compound (e.g., less than about 1-2% other media components or fermentation byproducts). When the desired compound is a hydroxyl fatty acid that has been derivatized to a salt, the compound is preferably further free (e.g., substantially free) of chemical contaminants associated with the formation of the salt. When the desired compound is a hydroxyl fatty acid that has been derivatized to an alcohol, the compound is preferably further free (e.g., substantially free) of chemical contaminants associated with the formation of the alcohol.

In an alternative embodiment, the desired hydroxyl fatty acid is not purified from the plant or microorganism, for example, when the plant or microorganism is biologically non-hazardous (e.g., safe). For example, the entire plant or culture (or culture supernatant) can be used as a source of product (e.g., crude product). In one embodiment, the plant or culture (or culture supernatant) supernatant is used without modification. In another embodiment, the plant or culture (or culture supernatant) is concentrated. In yet another embodiment, the plant or culture (or culture supernatant) is pulverized, dried, or lyophilized.

B. High Yield Production Methodologies

A particularly preferred embodiment of the present invention is a high yield production method for producing hydroxyl fatty acids, e.g., ricinoleic acid, comprising culturing a manipulated plant or microorganism under conditions such that the hydroxyl fatty acid is produced at a significantly high yield. The phrase "high yield production method," for example, a high yield production method for producing a desired compound (e.g., for producing a hydroxyl fatty acid) includes a method that results in production of the desired compound at a level which is elevated or above what is usual for comparable production methods. Preferably, a high yield production method results in production of the desired compound at a significantly high yield. The phrase "significantly high yield" includes a level of production or yield which is sufficiently elevated or above what is usual for comparable production methods, for example, which is elevated to a level sufficient for commercial production of the desired product (e.g., production of the product at a commercially feasible cost). In one embodiment, the invention features a high yield production method of producing hydroxyl fatty acids that includes culturing a manipulated plant or microorganism under conditions such that a hydroxyl fatty acid is produced at a level greater than 2 g/L. In another embodiment, the invention features a high yield production method of producing hydroxyl fatty acids that includes culturing a manipulated plant or microorganism under conditions such that a hydroxyl fatty acid is produced at a level greater than 10 g/L. In another embodiment, the invention features a high yield production method of producing hydroxyl fatty acids that includes culturing a manipulated plant or microorganism under conditions such that a hydroxyl fatty acid is produced at a level greater than 20 g/L. In yet another embodiment, the invention features a high yield production method of producing hydroxyl fatty acids that includes culturing a manipulated plant or microorganism under conditions such that a hydroxyl fatty acid is produced at a level greater than 30 g/L. In yet another embodiment, the invention features a high yield production method of producing hydroxyl fatty acids that includes culturing a manipulated plant or microorganism under conditions such that a hydroxyl fatty acid is produced at a level greater than 40 g/L.

The invention further features a high yield production method for producing a desired compound (e.g., for producing a hydroxyl fatty acid) that involves culturing a manipulated plant or microorganism under conditions such that a sufficiently elevated level of compound is produced within a commercially desirable period of time. In an exemplary embodiment, the invention features a high yield production method of producing hydroxyl fatty acids that includes culturing a manipulated plant or microorganism under conditions such that a hydroxyl fatty acid is produced at a level greater than 15-20 g/L in 36 hours. In another embodiment, the invention features a high yield production method of producing hydroxyl fatty acids that includes culturing a manipulated plant or microorganism under conditions such that a hydroxyl fatty acids produced at a level greater than 25-30 g/L in 48 hours. In another embodiment, the invention features a high yield production method of producing hydroxyl fatty acids that includes culturing a manipulated plant or microorganism under conditions such that a hydroxyl fatty acids produced at a level greater than 35-40 g/L in 72 hours, for example, greater that 37 g/L in 72 hours. In another embodiment, the invention features a high yield production method of producing hydroxyl fatty acids that includes culturing a manipulated plant or microorganism under conditions such that a hydroxyl fatty acid is produced at a level greater than 30-40 g/L in 60 hours, for example, greater that 30, 35 or 40 g/L in 60 hours. Values and ranges included and/or intermediate within the ranges set forth herein are also intended to be within the scope of the present invention. For example, hydroxyl fatty acid production at levels of at least 31, 32, 33, 34, 35, 36, 37, 38 and 39 g/L in 60 hours are intended to be included within the range of 30-40 g/L in 60 hours. In another example, ranges of 30-35 g/L or 35-40 g/L are intended to be included within the range of 30-40 g/L in 60 hours. Moreover, the skilled artisan will appreciate that culturing a manipulated microorganism to achieve a production level of, for example, "30-40 g/L in 60 hours" includes culturing the microorganism for additional time periods (e.g., time periods longer than 60 hours), optionally resulting in even higher yields of a hydroxyl fatty acid being produced.

IV. Compositions

The hydroxylase nucleic acid molecules, proteins, and fragments thereof, of the invention can be used to produce hydroxyl fatty acids which can be incorporated into compositions. Compositions of the present invention include, e.g., biolubricants, functional fluids, ink, paints, coatings, nylons, resins, foams and other biopolymers (see Jaworski and Cahoon (2003), the entire contents of which are hereby expressly incorporated by reference herein.

This invention is further illustrated by the following examples which should not be construed as limiting. The contents of all references, patents and published patent applications cited throughout this application, as well as the figures, are incorporated herein by reference.

EXAMPLES

Example 1

Organisms and Culture Conditions

*C. purpurea*, provided by Dr. Yu Chen, Department of Plant Science, University of Manitoba, was grown at 25° C. for 14 days in medium C (Mantle and Nisbet, 1976). *S. cerevisiae* strain InvSc1 (Invitrogen, Carlsbad, Calif.) was used as a heterologous host to express the *C. purpurea* CpFAH hydroxylase. Yeast cells were grown at 28° C. either in complex medium (YPD) or synthetic minimal medium (SD).

Example 2

Identification and Cloning of CpFAH hydroxylase cDNA

*C. purpurea* was reported to be capable of producing ricinoleic acid (12OH-18:1-9) in its sclerotia. To elucidate the mechanism underlying the biosynthesis of this hydroxyl fatty acid, we undertook a degenerate RT-PCR cloning strategy. We designed two degenerate primers that were targeted to conserved regions of $\Delta^{12}$ desaturases from fungi. By using this approach, we identified several $\Delta^{12}$ desaturase-like genes from the ricinoleate-producing tissues.

For reverse transcription-polymerase chain reaction (RT-PCR) experiments, the single stranded cDNA was synthesized by Superscript III reverse transcriptase (Invitrogen, Carlsbad, Calif.) using total RNAs from sclerotium-forming mycelia of *C. purpurea*. The cDNA was then used as the template for the PCR reaction with two degenerate oligonucleotide primers (DM34: 5'-GCICAYGARTGYGGICAYSRIGCITT-3' (SEQ ID NO: 9) and DM36: 5'-TAIGTDATIGCI ACIARCCARTGRTKIACCCA-3' (SEQ ID NO: 10)). These primers were designed based on the conserved amino acid regions of $\Delta^{12}$ hydroxylase and related proteins. The forward primer was in the first conserved histidine box and the reverse primer was outside the histidine boxes corresponding to the amino acid sequences WV(N/H)HWLVAITY (SEQ ID NO: 11). To obtain the entire sequences of the cDNA, the 5' and 3' regions were amplified separately using the Marathon cDNA Amplification Kit (BD Biosciences Clontech, Mountain View, Calif.) according to the manufacturer's instructions. The complete sequences including untranslated region were then amplified using specific primers DM61 (5'-CACTAGGGCAACGAATTACTCTGC-3' (SEQ ID NO: 12)) and DM62 (5'-GGACG CCATCGTTGACTTCC-3' (SEQ ID NO: 13)) by Pfx DNA polymerase (Invitrogen, Carlsbad, Calif.). The resulting bands were gel-purified, cloned into a pCR4-TOPO-TA cloning vector (Invitrogen, Carlsbad, Calif.) and sequenced.

The open reading frame of the gene encodes a protein of 477 amino acids in length (FIG. 1). Sequence comparison revealed that CpFAH shares 40% and 39% of amino acid identity with oleate hydroxylase from castor bean and *Lesquerella fendleri*, respectively. Higher homology of CpFAH was found to Δ12 desaturases from fungal *Gibberella fujukuroi* and *A. nidulans* (68% and 61%, respectively) (FIG. 2).

Example 3

Transformation of *S. cerevisiae* (Yeast) with CpFAH and Subsequent Culturing of the Transformed Strain The coding region of the cDNA was amplified by PCR using the Pfx DNA polymerase (Invitrogen, Carlsbad, Calif.) with primers DM63 (5'-GCGAATTCGAAATGGCTTCCGCTACTCC-3' (SEQ ID NO: 14)) and DM64 (5'-GCGAATTCCTACTGAGTC TTCATTGAAATGG-3' (SEQ ID NO: 15)) and cloned directly into pYES2.1 Topo-TA expression vector (Invitrogen, Carlsbad, Calif.) after Taq DNA polymerase treatment. The sequence of the insert was confirmed to be identical to the original cDNA and in the sense orientation relative to the GAL1 promoter.

*S. cerevisiae* strain InvSc1 was transformed with the construct using the S. C. EasyComp Transformation Kit (Invitrogen, Carlsbad, Calif.) with selection on uracil-deficient medium. For assessing the hydroxylase activity, recombinant yeast cells were grown to saturation in 25-ml cultures for 48 h at 28° C. on minimal medium (synthetic dropout) lacking uracil. The cultures were then washed and used to inoculate 25 ml of induction medium containing 2% galactose. Cultures were incubated at 20° C. for 3 days. INVSc1 yeast containing the empty plasmid vector pYES2.1 was used as a negative control.

Results and Discussion: Expression of CpFAH in Yeast Resulted in the Production of Ricinoleic Acid Transformants containing CpFAH produced several novel fatty acids compared to the control yeast. However, the most abundant fatty acid produced in the transformants had the retention time identical to standard ricinoleic acid and accounted for 15% of total fatty acids (FIG. 3). Mass spectrometry of the derivative of this novel peak showed that it produced an equivalent mass spectrum to that of derivatized ricinoleate (FIG. 4). Three characteristic ions with m/z values 187, 270, and 299 correspond to the three major fragmentation of TMS-methylricinoleate (FIG. 4). Thus, on the basis of chromatographic retention and mass spectrum, the novel fatty acid was unambiguously identified as ricinoleic acid. These data indicate that CpFAH is an oleate hydroxylase from *C. purpurea* capable of introducing a hydroxyl group at position 12 of oleic acid. The other two new fatty acids produced in transgenic yeast were identified as 16:2-9, 12 and 18:2-9, 12. These results indicate CpFAH is a bifunctional enzyme with $\Delta^{12}$ desaturase and hydroxylase activities and that the activity of hydroxylase is higher than that of $\Delta^{12}$ desaturase.

Example 4

Fatty Acid Analysis

For fatty acid analysis, yeast cells were pelleted by centrifugation, washed once with 0.1% tergitol and once with water. The fatty acids were converted to their methyl esters with 3 N methanolic HCl at 80° C. for 1 hour. After the addition of 1 mL of water, the sample was extracted twice with 2 mL of hexane. The hexane extract was combined and dried under $N_2$, and resuspended in 200 µL of hexane and analyzed on a Hewlett-Packard 5890A gas chromatograph equipped with a DB-23 column (30-m×0.25-mm×0.25-µm). The temperature program was isothermal 160° C. for 1 min, gradient 4° C./min to 240° C., and then isothermal at 240° C. for 10 min. For GC/MS analysis of TMS-recinoleate methyl ester, the 200 µL of ricinoleic methyl ester were dried under a stream of nitrogen and the residue was dissolved in 100 µL of N,O-bis(trimethylsilyl)acetamide (BSA; Aldrich)/pyridine (1:1). GC/MS analysis was accomplished using an Agilent 5973 mass selective detector coupled to an Agilent 6890N gas chromatograph using G1701DA MSD Chemstation software (for instrument control and data analysis) and equipped with a 30-m×0.25-mm DB-23 column with 0.25-µm film thickness (J&W Scientific, Folsom, Calif.). The chromatograph conditions included a split injection (20:1) onto the column using a helium flow of 0.4 ml/min, an initial temperature of 160° C. for 1 min, and a subsequent temperature ramp of 4° C./min to 240° C. The mass selective detector was run under standard electron impact conditions (70 eV), scanning an effective m/z range of 40-700 at 2.26 scans/s.

Example 5

Expression of CpFAH in Plants

To produce ricinoleic acid in plants, the CpFAH cDNA was expressed in *Arabidopsis thaliana* under the control of seed-specific *Brassica napus* napin storage protein promoter. The binary vectors (FIG. 5) containing the candidate gene was introduced by the in-planta *Agrobacterium*-infiltration approach into an *A. thaliana* double mutant (fad2fae1) that is unable to synthesize 20:1-11 and 18:2-9, 12 from 18:1-9, and accumulate a high level of oleic acid. By using this approach, 16 transgenic plants were produced. Fatty acid analysis of single seeds indicated the *C. purpurea* hydroxylase is highly active in *A. thaliana*. As shown in FIG. 6, compared to the untransformed mutant, transgenic *A. thaliana* produced three new fatty acids, 18:2-9, 12, 12-hydroxyl-18:1-9 and 12-hydroxyl-18:2-9, 15. Among them, 12-hydroxyl-18:1-9 is the most abundant, followed by 18:2-9, 12 and 12-hydroxyl-18:2-9, 15. The production of hydroxyl fatty acids is depicted in Table 1:

TABLE 1

Hydroxyl fatty acid production in *Arabidopsis thaliana* strains

| Fatty acid analysis (wt %) | 16:0 | 18:0 | 18:1-9c | 18:1-11c | 18:2 | 18:3 | 20:0 | 20:1 | 18:1-OH | 18:2-OH | Sum of Hydroxy FAs |
|---|---|---|---|---|---|---|---|---|---|---|---|
| fad2fae1-control-1 | 4.82 | 3.37 | 82.53 | 3.12 | 1.96 | 2.3 | 1.14 | 0.76 | 0 | 0 | 0 |
| fad2fae1-control-2 | 6.17 | 4.43 | 79.67 | 3.21 | 2.35 | 2.49 | 1.02 | 0.65 | 0 | 0 | 0 |
| castor bean | 3.36 | 6.05 | 60.91 | 4.19 | 2.39 | 1.57 | 0.9 | 0 | 15.32 | 5.31 | 20.63 |
| fad2fae1/4-6 | 7.36 | 6.61 | 44.81 | 4.42 | 9.65 | 3.37 | 0 | 0 | 17.85 | 5.93 | 23.78 |
| fad2fae1/6-4 | 12.76 | 10.87 | 22.58 | 13.8 | 14.43 | 3.97 | 1.15 | 0 | 19.24 | 1.19 | 20.43 |
| fad2fae1/7-5 | 7 | 9.61 | 40.77 | 4.8 | 10.16 | 3.71 | 1.03 | 0 | 17.5 | 5.42 | 22.92 |
| fad2fae1/8-2 | 12.86 | 15.54 | 25 | 6.25 | 16.25 | 4.64 | 0 | 0 | 16.96 | 2.5 | 19.46 |
| fad2fae1/9-7 | 2.67 | 9.37 | 37.9 | 5.77 | 11.5 | 3.93 | 0 | 0 | 23.55 | 5.27 | 28.82 |
| fad2fae1/10-1 | 5.78 | 9.74 | 39.96 | 5.38 | 10.65 | 3.55 | 1.12 | 0 | 19.37 | 4.46 | 23.83 |
| fad2fae1/11-4 | 9.23 | 7.86 | 41.16 | 5.3 | 11.59 | 3.73 | 0 | 0 | 16.8 | 4.32 | 21.12 |
| fad2fae1/13-3 | 9.26 | 8.56 | 41.98 | 5.25 | 11.81 | 3.63 | 0.85 | 0 | 14.74 | 3.94 | 18.68 |
| fad2fae1/14-5 | 9.93 | 7.25 | 44.9 | 4.35 | 9.54 | 4.05 | 0.73 | 0 | 13.52 | 5.73 | 19.25 |
| fad2fae1/15-7 | 3.07 | 6.34 | 42.6 | 4.85 | 10.44 | 3.2 | 0 | 0 | 23.2 | 6.3 | 29.5 |
| fad2fae1/16-3 | 3.92 | 6.2 | 43.17 | 5.15 | 9.42 | 3.94 | 0 | 0 | 19.89 | 8.31 | 28.2 |

The highest level of ricinoleic acid in transgenic *A. thaliana* accounted for 23.5% of the total fatty acid in seeds. The total hydroxyl fatty acids (12-hydroxyl-18:1-9 and 12-hydroxyl-18:2-9, 15) reached up to approximately 30% of the total fatty acid in seeds. These results further indicate, in part, that CpFAH is a bifunctional enzyme with $\Delta^{12}$ desaturase and hydroxylase activities and that the activity of hydroxylase is higher than that of $\Delta^{12}$ desaturase.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCE LIST

Billault, I., Mantle, P. G., and Robins, R. J. (2004). Deuterium NMR used to indicate a common mechanism for the biosynthesis of ricinoleic acid by *Ricinus communis* and *Claviceps purpurea*. J. Am. Chem. Soc. 126, 3250-3256.

Broun, P., Boddupalli, S., and Somerville, C. (1998). A bifunctional oleate 12-hydroxylase: desaturase from *Lesquerella fendleri*. Plant J. 13, 201-210.

Broun, P. and Somerville, C. (1997). Accumulation of ricinoleic, lesquerolic, and densipolic acids in seeds of transgenic *Arabidopsis* plants that express a fatty acyl hydroxylase cDNA from castor bean. Plant Physiol 113, 933-942.

Jaworski, J. and Cahoon, E. B. (2003). Industrial oils from transgenic plants. Curr. Opin. Plant Biol. 6, 178-184.

Mantle, P. G. and Nisbet, L. J. (1976). Differentiation of *Claviceps purpurea* in axenic culture. J. Gen. Microbiol. 93, 321-334.

Mey, G., Oeser, B., Lebrun, M. H., and Tudzynski, P. (2002). The biotrophic, non-appressorium-forming grass pathogen *Claviceps purpurea* needs a Fus3/Pmk1 homologous mitogen-activated protein kinase for colonization of rye ovarian tissue. Mol. Plant. Microbe Interact. 15, 303-312.

Morris, L. J., Hall, S. W., and James, A. T. (1966). The biosynthesis of ricinoleic acid by *Claviceps purpurea*. Biochem. J. 100, 29C-30C.

Smith, M. A., Moon, H., Chowrira, G., and Kunst, L. (2003). Heterologous expression of a fatty acid hydroxylase gene in developing seeds of *Arabidopsis thaliana*. Planta 217, 507-516.

Tudzynski, P., Correia, T., and Keller, U. (2001). Biotechnology and genetics of ergot alkaloids. Appl. Microbiol. Biotechnol. 57, 593-605.

van de Loo, F. J., Broun, P., Turner, S., and Somerville, C. (1995). An oleate 12-hydroxylase from *Ricinus communis* L. is a fatty acyl desaturase homolog. Proc. Natl. Acad. Sci. U.S.A 92, 6743-6747.

What is claimed:

1. An isolated nucleic acid molecule selected from the group consisting of
   a) an isolated nucleic acid molecule comprising the nucleotide sequence of SEQ ID NO:1, or the full complement thereof;
   b) an isolated nucleic acid molecule which encodes a polypeptide comprising the amino acid sequence of SEQ ID NO:2, or the full complement thereof;
   c) an isolated nucleic acid molecule comprising a nucleotide sequence which is at least 85% identical to the entire nucleotide sequence of SEQ ID NO:1, or the full complement thereof;
   d) an isolated nucleic acid molecule comprising a nucleotide sequence which hybridizes to the complement of the nucleotide sequence of SEQ ID NO:1 in 4× sodium chloride/sodium citrate (SSC), at about 65-70° C., followed by one or more washes in 1×SSC, at about 65-70° C., or the full complement thereof;
   e) an isolated nucleic acid molecule comprising a fragment of at least 25 contiguous nucleotides of the nucleotide sequence of SEQ ID NO:1, or the full complement thereof; and
   f) an isolated nucleic acid molecule which encodes a polypeptide comprising an amino acid sequence which is at least 85% identical to the entire amino acid sequence of SEQ ID NO:2, or the full complement thereof.

2. The isolated nucleic acid molecule of claim 1, wherein said nucleic acid molecule encodes a fatty acid hydroxylase protein having an activity of catalyzing the introduction of a hydroxyl group in a fatty acid.

3. The isolated nucleic acid molecule of claim 1, wherein said nucleic acid molecule encodes a fatty acid desaturase protein having an activity of catalyzing the introduction of a double bond in a fatty acid.

4. An isolated nucleic acid molecule comprising the nucleic acid molecule of claim 1 and a nucleotide sequence encoding a heterologous polypeptide.

5. A vector comprising the nucleic acid molecule of claim 1.

6. The vector of claim 5, which is an expression vector.

7. An isolated host cell transformed with the expression vector of claim 6.

8. The host cell of claim 7, wherein said cell is a plant cell or a microbial cell.

9. The host cell of claim 8, wherein said plant cell is a cell obtained from an oilseed crop.

10. The host cell of claim 9, wherein the oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla.

11. The host cell of claim 8, wherein the microbial cell is selected from the group consisting of *Candida, Cryptococcus, Lipomyces, Rhodosporidium, Yarrowia, Thraustochytrium, Pythium, Schizochytrium* and *Crythecodinium*.

12. The host cell of claim 7, wherein the cell is derived from *Saccharomyces cerevisiae*.

13. A method of producing a polypeptide comprising culturing the host cell of claim 7 in an appropriate culture medium to, thereby, produce the polypeptide, wherein the polypeptide is at least one of a fatty acid hydroxylase protein having an activity of catalyzing the introduction of a hydroxyl group in a fatty acid or a fatty acid desaturase protein having an activity of catalyzing the introduction of a double bond in a fatty acid.

14. A method for producing a hydroxyl fatty acid, comprising culturing the cell of claim 7 such that the hydroxyl fatty acid is produced.

15. A method of modulating the production of a hydroxyl fatty acid comprising culturing the cell of claim 7, such that modulation of the production of a hydroxyl fatty acid occurs.

16. The method of claim 15, wherein the production of the hydroxyl fatty acid is enhanced.

17. A method for the large-scale production of a hydroxyl fatty acid comprising culturing the cell of claim 7, such that the production of the hydroxyl fatty acid occurs.

18. A plant comprising the vector of claim 6.

19. A seed produced by the plant of claim 18.

20. The vector of claim 5, wherein the nucleic acid molecule is under the control of a seed-specific promoter.

21. The vector of claim 20, wherein the seed-specific promoter is selected from the group consisting of Conlinin 1, Conlinin 2, napin and LuFad3 or other seed-specific promoters.

22. A method of producin a hydroxyl fatty acid comprising contacting a composition comprising at least one hydroxylase target molecule with at least one polypeptide encoded by the nucleic acid molecule of claim 1 under conditions such that the hydroxyl fatty acid is produced.

23. The method of claim 22, wherein the hydroxylase target molecule is octadec-9-enioc acid (oleic acid).

24. A method of producing a cell capable of generating a hydroxyl fatty acid comprising introducing into said cell the nucleic acid molecule of claim 1, wherein the nucleic acid molecule encodes a hydroxylase having an activity of catalyzing the introduction of a hydroxyl group in a fatty acid.

25. The isolated nucleic acid molecule of claim 1, wherein the nucleic acid molecule comprises the nucleotide sequence of SEQ ID NO:1, or the full complement thereof.

26. The isolated nucleic acid molecule of claim 1, wherein the nucleic acid molecule encodes a polypeptide comprising the amino acid sequence of SEQ ID NO:2, or the full complement thereof.

27. The isolated nucleic acid molecule of claim 1, wherein the nucleic acid molecule comprises a nucleotide sequence which is at least 85% identical to the entire nucleotide sequence of SEQ ID NO:1, or the full complement thereof.

28. The nucleic acid molecule of claim 27, wherein the nucleic acid molecule comprises a nucleotide sequence which is at least 90% identical to the entire nucleotide sequence of SEQ ID NO:1.

29. The nucleic acid molecule of claim 27, wherein the nucleic acid molecule comprises a nucleotide sequence which is at least 95% identical to the entire nucleotide sequence of SEQ ID NO:1.

30. The isolated nucleic acid molecule of claim 1, wherein the nucleic acid molecule comprises a nucleotide sequence which hybridizes to the complement of the nucleotide sequence of SEQ ID NO:1 in 4X sodium chloride/sodium citrate (SSC), at about 65-70° C., followed by one or more washes in 1X SSC, at about 65-70° C., or the full complement thereof.

31. The isolated nucleic acid molecule of claim 1, wherein the nucleic acid molecule comprises a fragment of at least 25 contiguous nucleotides of the nucleotide sequence of SEQ ID NO:1, or the full complement thereof.

32. The isolated nucleic acid molecule of claim 1, wherein the nucleic acid molecule encodes a polypeptide comprising an amino acid sequence which is at least 85% identical to the entire amino acid sequence of SEQ ID NO:2, or the full complement thereof.

33. The nucleic acid molecule of claim 32, wherein the polypeptide comprises an amino acid sequence which is at least 90% identical to the entire amino acid sequence of SEQ ID NO:2.

34. The nucleic acid molecule of claim 32, wherein the polypeptide comprises an amino acid sequence which is at least 95% identical to the entire amino acid sequence of SEQ ID NO:2.

35. The nucleic acid molecule of claim 1(c), wherein the nucleic acid molecule comprises a nucleotide sequence which is at least 95% identical to the entire nucleotide sequence of SEQ ID NO:1.

36. The nucleic acid molecule of claim 1(f), wherein the polypeptide comprises an amino acid sequence which is at least 90% identical to the entire amino acid sequence of SEQ ID NO:2.

37. The nucleic acid molecule of claim 1(f), wherein the polypeptide comprises an amino acid sequence which is at least 95% identical to the entire amino acid sequence of SEQ ID NO:2.

38. The method of claim 37, wherein said plant cell is a cell obtained from an oilseed crop.

39. The method of claim 38, wherein the oilseed crop is selected from the group consisting of flax (*Linum sp.*), rapeseed (*Brassica sp.*), soybean (*Glycine and Soja sp.*), sunflower (*Helianthus sp.*), cotton (*Gossypium sp.*), corn (*Zea mays*), olive (*Olea sp.*), safflower (*Carthamus sp.*), cocoa (*Theobroma cacoa*), peanut (*Arachis sp.*), hemp, camelina, crambe, oil palm, coconuts, groundnuts, sesame seed, castor bean, lesquerella, tallow tree, sheanuts, tungnuts, kapok fruit, poppy seed, jojoba seeds and perrilla.

40. The method of claim 37, wherein said cell is *Brassica juncea*.

41. The method of claim 37, wherein the microbial cell is selected from the group consisting *Candida, Cryptococcus, Lipomyces, Rhodosporidium, Yarrowia, Thraustochytrium, Pythium, Schizochytrium* and *Crythecodinium*.

42. The method of any one of claims 14, 24, 15 or 17 wherein said cell is derived from *Saccharmoyces cerevisiae*.

43. The method of claim 14, 24, 17 wherein expression of the nucleic acid molecule results in modulation of production of said hydroxyl fatty acid.

\* \* \* \* \*

UNITED STATES PATENT AND TRADEMARK OFFICE
CERTIFICATE OF CORRECTION

PATENT NO. : 7,923,598 B2
APPLICATION NO. : 11/767115
DATED : April 12, 2011
INVENTOR(S) : Meesapyodsuk et al.

It is certified that error appears in the above-identified patent and that said Letters Patent is hereby corrected as shown below:

On the Title page:

In Item (56) for Cited References, with respect to the Van de Loo reference in the right column, replace "communisL." with --communis L.--; and replace "U. S. A" with --USA--.

In the Claims:

In claim 1 d), at column 45, lines 48 and 50, replace "° C." with --°C--.

In claim 22, at column 47, line 21, replace "producin" with --producing--.

In claim 23, at column 47, line 27, replace "octadec-9-enioc" with --octadec-9-enoic--.

In claim 30, at column 48, lines 1 and 2, replace "° C." with --°C--.

In claim 35, at column 48, lines 21-24, replace "The nucleic acid molecule of claim 1(c), wherein the nucleic acid molecule comprises a nucleotide sequence which is at least 95% identical to the entire nucleotide sequence of SEQ ID NO:1." with --The method of any one of claims 14, 15, 17, 22 and 24, wherein said method further comprises the step of recovering the hydroxyl fatty acid from said culture.--.

In claim 36, at column 48, lines 25-28, replace "The nucleic acid molecule of claim 1(f), wherein the polypeptide comprises an amino acid sequence which is at least 90% identical to the entire amino acid sequence of SEQ ID NO:2." with --The method of any one of claims 14, 15, 17, 22 and 24, wherein said hydroxyl fatty acid is 12-hydroxyoctadec-9-enoic acid (ricinoleic acid).--.

Signed and Sealed this
Twenty-seventh Day of March, 2012

David J. Kappos
*Director of the United States Patent and Trademark Office*

CERTIFICATE OF CORRECTION (continued)
U.S. Pat. No. 7,923,598 B2

In claim 37, at column 48, lines 29-32, replace "The nucleic acid molecule of claim 1(f), wherein the polypeptide comprises an amino acid sequence which is at least 95% identical to the entire amino acid sequence of SEQ ID NO:2." with --The method of any one of claims 14, 15, 17 and 24, wherein said cell is a plant cell or a microbial cell.--.

In claim 42, at column 48, line 51, replace "*Saccharmoyces*" with --*Saccharomyces*--.

In claim 43, at column 48, line 52, replace "24, 17" with --24 or 17--.

SEQUENCE LISTING

```
<160> NUMBER OF SEQ ID NOS: 15

<210> SEQ ID NO 1
<211> LENGTH: 1434
<212> TYPE: DNA
<213> ORGANISM: Claviceps purpurea
<220> FEATURE:
<221> NAME/KEY: CDS
<222> LOCATION: (1)..(1431)

<400> SEQUENCE: 1 atg gct tcc gct act cct gca atg tca gaa aac gca gtt ctg cgg cac      48
Met Ala Ser Ala Thr Pro Ala Met Ser Glu Asn Ala Val Leu Arg His
  1               5                  10                  15 aag gcg gcc tcg acg act ggc atc gat tac gaa tcg tcg gcc gct gtc      96
Lys Ala Ala Ser Thr Thr Gly Ile Asp Tyr Glu Ser Ser Ala Ala Val
             20                  25                  30 agt cca gcc gaa tcg cct aga acc tca gcc tcg tct aca tcg ctt tcg     144
Ser Pro Ala Glu Ser Pro Arg Thr Ser Ala Ser Ser Thr Ser Leu Ser
         35                  40                  45 tca ctt tct tct ctc gac gct aat gaa aag aaa gac gag tac gcc ggc     192
Ser Leu Ser Ser Leu Asp Ala Asn Glu Lys Lys Asp Glu Tyr Ala Gly
     50                  55                  60 ctc ctt gat acg tac gga aac gcc ttc acg ccc cct gac ttc agc atc     240
Leu Leu Asp Thr Tyr Gly Asn Ala Phe Thr Pro Pro Asp Phe Ser Ile
 65                  70                  75                  80 aaa gac atc cgc gct gcc att ccc aag cat tgc tac gaa cgc tct acc     288
Lys Asp Ile Arg Ala Ala Ile Pro Lys His Cys Tyr Glu Arg Ser Thr
                 85                  90                  95 atc aag agc tac gca tat gtt ctt cgc gat ctc ctc tgt ctt tcg act     336
Ile Lys Ser Tyr Ala Tyr Val Leu Arg Asp Leu Leu Cys Leu Ser Thr
            100                 105                 110 acg ttc tac ctg ttc cac aac ttc gta acg cca gag aac ata cca tcc     384
Thr Phe Tyr Leu Phe His Asn Phe Val Thr Pro Glu Asn Ile Pro Ser
        115                 120                 125 aac ccc ctt cgt ttc gtg ctc tgg agc atc tac aca gta ctg caa ggt     432
Asn Pro Leu Arg Phe Val Leu Trp Ser Ile Tyr Thr Val Leu Gln Gly
    130                 135                 140 ctc ttt gcg acc gga ctt tgg gtc att ggt cat gaa tgt ggt cac tgt     480
Leu Phe Ala Thr Gly Leu Trp Val Ile Gly His Glu Cys Gly His Cys
145                 150                 155                 160 gcc ttt tcc ccg tct ccc ttt atc agc gac ctc acc ggc tgg gtc att     528
Ala Phe Ser Pro Ser Pro Phe Ile Ser Asp Leu Thr Gly Trp Val Ile
                165                 170                 175 cac tca gct ctc ctc gtg cct tat ttc agt tgg aaa ttt tcc cac agt     576
His Ser Ala Leu Leu Val Pro Tyr Phe Ser Trp Lys Phe Ser His Ser
            180                 185                 190
```

| | | | | | | | | | | | | | | | | |
|---|---|---|---|---|---|---|---|---|---|---|---|---|---|---|---|---|
| gcc | cat | cac | aag | ggg | att | gga | aac | atg | gag | cgc | gac | atg | gtc | ttt | ctg | 624 |
| Ala | His | His | Lys | Gly | Ile | Gly | Asn | Met | Glu | Arg | Asp | Met | Val | Phe | Leu | |
| | 195 | | | | | 200 | | | | | 205 | | | | | |

```
gcc cat cac aag ggg att gga aac atg gag cgc gac atg gtc ttt ctg    624
Ala His His Lys Gly Ile Gly Asn Met Glu Arg Asp Met Val Phe Leu
        195                 200                 205 cct cgg aca cgc gag cag cag gcc act cga ctt gga cgc gcg gtc gag    672
Pro Arg Thr Arg Glu Gln Gln Ala Thr Arg Leu Gly Arg Ala Val Glu
210                 215                 220 gaa ctc ggc gat ctt tgc gag gag aca ccc att tac acg gct ctg cat    720
Glu Leu Gly Asp Leu Cys Glu Glu Thr Pro Ile Tyr Thr Ala Leu His
225                 230                 235                 240 ctg gtc ggt aag cag ctc atc ggt tgg ccc agc tac ctc atg acg aac    768
Leu Val Gly Lys Gln Leu Ile Gly Trp Pro Ser Tyr Leu Met Thr Asn
            245                 250                 255 gcc aca gga cac aat ttc cac gaa cgc cag cgg gag ggt cga ggc aag    816
Ala Thr Gly His Asn Phe His Glu Arg Gln Arg Glu Gly Arg Gly Lys
                260                 265                 270 ggc aag aag aac ggt ttc ggg ggg ggc gta aat cac ttt gat ccc cgc    864
Gly Lys Lys Asn Gly Phe Gly Gly Gly Val Asn His Phe Asp Pro Arg
        275                 280                 285 agc cct att ttc gaa gcc cga cag gcc aag tac att gtt ctc tct gac    912
Ser Pro Ile Phe Glu Ala Arg Gln Ala Lys Tyr Ile Val Leu Ser Asp
290                 295                 300 atc ggc ctg ggt ctt gcc atc gct gct ttg gta tac ctc ggc aac cga    960
Ile Gly Leu Gly Leu Ala Ile Ala Ala Leu Val Tyr Leu Gly Asn Arg
305                 310                 315                 320 ttc ggc tgg gcc aac atg gct gtc tgg tac ttt ttg ccc tat ctc tgg   1008
Phe Gly Trp Ala Asn Met Ala Val Trp Tyr Phe Leu Pro Tyr Leu Trp
            325                 330                 335 gtg aac cac tgg ctc gtt gcc att acg ttc ctc cag cac acg gat cca   1056
Val Asn His Trp Leu Val Ala Ile Thr Phe Leu Gln His Thr Asp Pro
                340                 345                 350 act ttg cct cat tac aat cgc gaa gag tgg aat ttt gtt cgt gga ggt   1104
Thr Leu Pro His Tyr Asn Arg Glu Glu Trp Asn Phe Val Arg Gly Gly
        355                 360                 365 gct tgc acc att gat cgt gac ttg ggc ttc att ggc cgc cat cta ttc   1152
Ala Cys Thr Ile Asp Arg Asp Leu Gly Phe Ile Gly Arg His Leu Phe
370                 375                 380 cac ggc att gct gat aca cat gtc gtc cat cat tat gtc agc cgc att   1200
His Gly Ile Ala Asp Thr His Val Val His His Tyr Val Ser Arg Ile
385                 390                 395                 400 cct ttc tat aat gct gac gaa gcc tcc gag gcg atc aag ccg atc atg   1248
Pro Phe Tyr Asn Ala Asp Glu Ala Ser Glu Ala Ile Lys Pro Ile Met
            405                 410                 415 ggc aag cac tat cgc tca gac acc gca cac ggt cct gtg gga ttc ctc   1296
Gly Lys His Tyr Arg Ser Asp Thr Ala His Gly Pro Val Gly Phe Leu
                420                 425                 430 cac gct ctt tgg aag act gct cgc tgg tgc cag tgg gta gag ccc agc   1344
His Ala Leu Trp Lys Thr Ala Arg Trp Cys Gln Trp Val Glu Pro Ser
        435                 440                 445 gcc gac gcc caa ggt gct ggc aag ggc atc tta ttc tac cgc aac cga   1392
Ala Asp Ala Gln Gly Ala Gly Lys Gly Ile Leu Phe Tyr Arg Asn Arg
450                 455                 460 aat aaa ctt ggt acg aag ccc att tca atg aag act cag tag           1434
Asn Lys Leu Gly Thr Lys Pro Ile Ser Met Lys Thr Gln
465                 470                 475
```

<210> SEQ ID NO 2
<211> LENGTH: 477
<212> TYPE: PRT
<213> ORGANISM: Claviceps purpurea

<400> SEQUENCE: 2

```
Met Ala Ser Ala Thr Pro Ala Met Ser Glu Asn Ala Val Leu Arg His
  1               5                  10                  15
Lys Ala Ala Ser Thr Thr Gly Ile Asp Tyr Glu Ser Ser Ala Ala Val
                 20                  25                  30
Ser Pro Ala Glu Ser Pro Arg Thr Ser Ala Ser Ser Thr Ser Leu Ser
             35                  40                  45
Ser Leu Ser Ser Leu Asp Ala Asn Glu Lys Lys Asp Glu Tyr Ala Gly
         50                  55                  60
Leu Leu Asp Thr Tyr Gly Asn Ala Phe Thr Pro Pro Asp Phe Ser Ile
 65                  70                  75                  80
Lys Asp Ile Arg Ala Ala Ile Pro Lys His Cys Tyr Glu Arg Ser Thr
                 85                  90                  95
Ile Lys Ser Tyr Ala Tyr Val Leu Arg Asp Leu Leu Cys Leu Ser Thr
                100                 105                 110
Thr Phe Tyr Leu Phe His Asn Phe Val Thr Pro Glu Asn Ile Pro Ser
            115                 120                 125
Asn Pro Leu Arg Phe Val Leu Trp Ser Ile Tyr Thr Val Leu Gln Gly
        130                 135                 140
Leu Phe Ala Thr Gly Leu Trp Val Ile Gly His Glu Cys Gly His Cys
145                 150                 155                 160
Ala Phe Ser Pro Ser Pro Phe Ile Ser Asp Leu Thr Gly Trp Val Ile
                165                 170                 175
His Ser Ala Leu Leu Val Pro Tyr Phe Ser Trp Lys Phe Ser His Ser
            180                 185                 190
Ala His His Lys Gly Ile Gly Asn Met Glu Arg Asp Met Val Phe Leu
        195                 200                 205
Pro Arg Thr Arg Glu Gln Gln Ala Thr Arg Leu Gly Arg Ala Val Glu
210                 215                 220
Glu Leu Gly Asp Leu Cys Glu Glu Thr Pro Ile Tyr Thr Ala Leu His
225                 230                 235                 240
Leu Val Gly Lys Gln Leu Ile Gly Trp Pro Ser Tyr Leu Met Thr Asn
                245                 250                 255
Ala Thr Gly His Asn Phe His Glu Arg Gln Arg Glu Gly Arg Gly Lys
            260                 265                 270
Gly Lys Lys Asn Gly Phe Gly Gly Val Asn His Phe Asp Pro Arg
        275                 280                 285
Ser Pro Ile Phe Glu Ala Arg Gln Ala Lys Tyr Ile Val Leu Ser Asp
        290                 295                 300
Ile Gly Leu Gly Leu Ala Ile Ala Ala Leu Val Tyr Leu Gly Asn Arg
305                 310                 315                 320
Phe Gly Trp Ala Asn Met Ala Val Trp Tyr Phe Leu Pro Tyr Leu Trp
                325                 330                 335
Val Asn His Trp Leu Val Ala Ile Thr Phe Leu Gln His Thr Asp Pro
            340                 345                 350
Thr Leu Pro His Tyr Asn Arg Glu Glu Trp Asn Phe Val Arg Gly Gly
        355                 360                 365
Ala Cys Thr Ile Asp Arg Asp Leu Gly Phe Ile Gly Arg His Leu Phe
        370                 375                 380
His Gly Ile Ala Asp Thr His Val Val His His Tyr Val Ser Arg Ile
385                 390                 395                 400
Pro Phe Tyr Asn Ala Asp Glu Ala Ser Glu Ala Ile Lys Pro Ile Met
                405                 410                 415
Gly Lys His Tyr Arg Ser Asp Thr Ala His Gly Pro Val Gly Phe Leu
            420                 425                 430
```

```
His Ala Leu Trp Lys Thr Ala Arg Trp Cys Gln Trp Val Glu Pro Ser
            435                 440                 445

Ala Asp Ala Gln Gly Ala Gly Lys Gly Ile Leu Phe Tyr Arg Asn Arg
450                 455                 460

Asn Lys Leu Gly Thr Lys Pro Ile Ser Met Lys Thr Gln
465                 470                 475

<210> SEQ ID NO 3
<211> LENGTH: 420
<212> TYPE: PRT
<213> ORGANISM: Aspergillus nidulans

<400> SEQUENCE: 3

Met Ala Ser Asp Ala Gly Lys Gly Asp Leu Gly Lys Met Leu Asp Thr
1               5                   10                  15

Tyr Gly Asn Glu Phe Lys Ile Pro Asp Tyr Thr Ile Lys Asp Ile Arg
            20                  25                  30

Asp Ala Ile Pro Ser His Cys Tyr Asn Arg Ser Ala Ile Arg Ser Leu
        35                  40                  45

Ser Tyr Val Phe Arg Asp Leu Ala Val Leu Ala Ser Val Phe Tyr Val
    50                  55                  60

Phe His Lys Tyr Val Thr Pro Glu Thr Val Pro Ser Tyr Pro Ala Arg
65                  70                  75                  80

Val Ala Leu Trp Thr Leu Tyr Thr Val Gln Gly Leu Phe Gly Thr
            85                  90                  95

Gly Ile Trp Val Leu Ala His Glu Cys Gly His Gln Ala Phe Ser Thr
        100                 105                 110

Ser Lys Val Leu Asn Asp Thr Val Gly Trp Ile Leu His Ser Ala Leu
    115                 120                 125

Leu Val Pro Tyr Phe Ser Trp Lys Ile Ser His Gly Lys His His Lys
130                 135                 140

Ala Thr Gly Asn Leu Ala Arg Asp Met Val Phe Val Pro Lys Thr Arg
145                 150                 155                 160

Glu Val Tyr Ala Ser Arg Ile Lys Lys Thr Ile Tyr Asp Leu Asn Glu
            165                 170                 175

Val Met Glu Glu Thr Pro Leu Ala Thr Ala Thr His Ser Ile Leu Gln
        180                 185                 190

Gln Leu Phe Gly Trp Pro Leu Tyr Leu Leu Thr Asn Val Thr Gly His
    195                 200                 205

Asp Asn His Glu Arg Gln Pro Glu Gly Arg Gly Lys Gly Lys Arg Asn
210                 215                 220

Gly Tyr Phe Thr Gly Val Asn His Phe Asn Pro Asn Ser Pro Leu Phe
225                 230                 235                 240

Glu Ala Lys Asp Ala Lys Leu Ile Ile Leu Ser Asp Ile Gly Leu Ala
            245                 250                 255

Ile Thr Ala Ser Ile Leu Tyr Leu Ile Gly Ser Lys Phe Gly Trp Met
        260                 265                 270

Asn Leu Leu Val Trp Tyr Gly Ile Pro Tyr Leu Trp Val Asn His Trp
    275                 280                 285

Leu Val Ala Ile Thr Tyr Leu Gln His Thr Asp Pro Thr Leu Pro His
290                 295                 300

Tyr Gln Pro Glu Ser Trp Thr Phe Ala Arg Gly Ala Ala Ala Thr Ile
305                 310                 315                 320

Asp Arg Glu Phe Gly Phe Ile Gly Arg His Ile Leu His Gly Ile Ile
            325                 330                 335
```

```
Glu Thr His Val Leu His His Tyr Val Ser Thr Ile Pro Phe Tyr His
                340                 345                 350

Ala Asp Glu Ala Ser Glu Ala Ile Lys Lys Val Met Gly Ser His Tyr
            355                 360                 365

Arg Ser Glu Ala His Thr Gly Pro Leu Gly Phe Leu Lys Ala Leu Trp
        370                 375                 380

Thr Ser Ala Arg Val Cys His Trp Val Glu Pro Thr Glu Gly Thr Lys
385                 390                 395                 400

Gly Glu Asn Ala Gly Val Leu Phe Phe Arg Asn Thr Asn Gly Ile Gly
                405                 410                 415

Val Pro Pro His
            420

<210> SEQ ID NO 4
<211> LENGTH: 384
<212> TYPE: PRT
<213> ORGANISM: Lesquerella fendleri

<400> SEQUENCE: 4

Met Gly Ala Gly Gly Arg Ile Met Val Thr Pro Ser Ser Lys Lys Ser
1               5                   10                  15

Glu Thr Glu Ala Leu Lys Arg Gly Pro Cys Glu Lys Pro Pro Phe Thr
            20                  25                  30

Val Lys Asp Leu Lys Lys Ala Ile Pro Gln His Cys Phe Lys Arg Ser
        35                  40                  45

Ile Pro Arg Ser Phe Ser Tyr Leu Leu Thr Asp Ile Thr Leu Val Ser
    50                  55                  60

Cys Phe Tyr Tyr Val Ala Thr Asn Tyr Phe Ser Leu Leu Pro Gln Pro
65                  70                  75                  80

Leu Ser Thr Tyr Leu Ala Trp Pro Leu Tyr Trp Val Cys Gln Gly Cys
                85                  90                  95

Val Leu Thr Gly Ile Trp Val Ile Gly His Glu Cys Gly His His Ala
            100                 105                 110

Phe Ser Asp Tyr Gln Trp Val Asp Asp Thr Val Gly Phe Ile Phe His
        115                 120                 125

Ser Phe Leu Leu Val Pro Tyr Phe Ser Trp Lys Tyr Ser His Arg Arg
    130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Ile Leu Val Leu Thr Val Gln Phe Ile Leu Gly Trp Pro
            180                 185                 190

Leu Tyr Leu Ala Phe Asn Val Ser Gly Arg Pro Tyr Asp Gly Phe Ala
        195                 200                 205

Ser His Phe Phe Pro His Ala Pro Ile Phe Lys Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Ser Gln Gly Leu Thr Ala Met Ile Cys Val Tyr
                245                 250                 255

Gly Val Pro Leu Leu Ile Val Asn Phe Phe Leu Val Leu Val Thr Phe
            260                 265                 270

Leu Gln His Thr His Pro Ser Leu Pro His Tyr Asp Ser Thr Glu Trp
        275                 280                 285
```

```
Glu Trp Ile Arg Gly Ala Leu Val Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ala Thr Ile Pro His Tyr Asn Ala Met Glu Ala Thr Glu Ala
                325                 330                 335

Ile Lys Pro Ile Leu Gly Asp Tyr Tyr His Phe Asp Gly Thr Pro Trp
            340                 345                 350

Tyr Val Ala Met Tyr Arg Glu Ala Lys Glu Cys Leu Tyr Val Glu Pro
        355                 360                 365

Asp Thr Glu Arg Gly Lys Lys Gly Val Tyr Tyr Tyr Asn Asn Lys Leu
    370                 375                 380

<210> SEQ ID NO 5
<211> LENGTH: 387
<212> TYPE: PRT
<213> ORGANISM: Ricinus communis

<400> SEQUENCE: 5

Met Gly Gly Gly Gly Arg Met Ser Thr Val Ile Thr Ser Asn Asn Ser
  1               5                  10                  15

Glu Lys Lys Gly Gly Ser Ser His Leu Lys Arg Ala Pro His Thr Lys
             20                  25                  30

Pro Pro Phe Thr Leu Gly Asp Leu Lys Arg Ala Ile Pro Pro His Cys
         35                  40                  45

Phe Glu Arg Ser Phe Val Arg Ser Phe Ser Tyr Val Ala Tyr Asp Val
     50                  55                  60

Cys Leu Ser Phe Leu Phe Tyr Ser Ile Ala Thr Asn Phe Phe Pro Tyr
 65                  70                  75                  80

Ile Ser Ser Pro Leu Ser Tyr Val Ala Trp Leu Val Tyr Trp Leu Phe
                 85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
    130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Ser
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
    210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285
```

```
Ser Glu Trp Asp Trp Leu Arg Gly Ala Met Val Thr Val Asp Arg Asp
        290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 6
<211> LENGTH: 6
<212> TYPE: PRT
<213> ORGANISM: Unknown Organism
<220> FEATURE:
<223> OTHER INFORMATION: Description of Unknown Organism: Conserved
      amino acid domain derived from various organism sources

<400> SEQUENCE: 6

Gly His Glu Cys Gly His
 1               5

<210> SEQ ID NO 7
<211> LENGTH: 5
<212> TYPE: PRT
<213> ORGANISM: Unknown Organism
<220> FEATURE:
<223> OTHER INFORMATION: Description of Unknown Organism: Conserved
      amino acid domain derived from various organism sources

<400> SEQUENCE: 7

His Ser Ala His His
 1               5

<210> SEQ ID NO 8
<211> LENGTH: 5
<212> TYPE: PRT
<213> ORGANISM: Unknown Organism
<220> FEATURE:
<223> OTHER INFORMATION: Description of Unknown Organism: Conserved
      amino acid domain derived from various organism sources

<400> SEQUENCE: 8

His Val Val His His
 1               5

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: Inosine
<220> FEATURE:
<221> NAME/KEY: modified_base
<222> LOCATION: (15)
<223> OTHER INFORMATION: Inosine
```

```
<220> FEATURE:
<221> NAME/KEY: modified_base
<222> LOCATION: (21)
<223> OTHER INFORMATION: Inosine
<220> FEATURE:
<221> NAME/KEY: modified_base
<222> LOCATION: (24)
<223> OTHER INFORMATION: Inosine

<400> SEQUENCE: 9
gcncaygart gyggncaysr ngcntt                                              26

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: Inosine
<220> FEATURE:
<221> NAME/KEY: modified_base
<222> LOCATION: (9)
<223> OTHER INFORMATION: Inosine
<220> FEATURE:
<221> NAME/KEY: modified_base
<222> LOCATION: (12)
<223> OTHER INFORMATION: Inosine
<220> FEATURE:
<221> NAME/KEY: modified_base
<222> LOCATION: (15)
<223> OTHER INFORMATION: Inosine
<220> FEATURE:
<221> NAME/KEY: modified_base
<222> LOCATION: (27)
<223> OTHER INFORMATION: Inosine

<400> SEQUENCE: 10
tangtdatng cnacnarcca rtgrtknacc ca                                       32

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Asn or His

<400> SEQUENCE: 11

Trp Val Xaa His Trp Leu Val Ala Ile Thr Tyr
  1               5                  10

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cactagggca acgaattact ctgc                                                24

<210> SEQ ID NO 13
<211> LENGTH: 20
```

```
                                        -continued
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggacgccatc gttgacttcc                                                      20

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgaattcga aatggcttcc gctactcc                                             28

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcgaattcct actgagtctt cattgaaatg g                                         31
```